United States Patent
Matsubara et al.

(10) Patent No.: US 9,677,127 B2
(45) Date of Patent: Jun. 13, 2017

(54) METHOD OF DETECTING GENE MUTATION

(75) Inventors: Yoichi Matsubara, Sendai (JP); Shigeo Kure, Sendai (JP)

(73) Assignee: SEKISUI MEDICAL CO., LTD., Tokyo (JP)

(*) Notice: Subject to any disclaimer, the term of this patent is extended or adjusted under 35 U.S.C. 154(b) by 781 days.

(21) Appl. No.: 12/119,141

(22) Filed: May 12, 2008

(65) Prior Publication Data

US 2008/0318238 A1  Dec. 25, 2008

Related U.S. Application Data

(63) Continuation of application No. 10/533,750, filed as application No. PCT/JP03/14204 on Nov. 7, 2003, now abandoned.

(30) Foreign Application Priority Data

Nov. 7, 2002 (JP) .................................. 2002-323419

(51) Int. Cl.
C12Q 1/68 (2006.01)

(52) U.S. Cl.
CPC ................................. *C12Q 1/6827* (2013.01)

(58) Field of Classification Search
CPC  C12Q 2531/113; C12Q 1/6851; C12Q 1/686; C12Q 1/6816; C12Q 1/6827; C12Q 1/6837; C12Q 1/6874; C12Q 1/6818; C12Q 1/6844; C12Q 1/682; C12Q 2525/16; C12Q 2561/101; C12Q 2561/113; C12Q 2600/156; C12Q 2600/58; C12Q 2563/107; C12Q 2527/107

See application file for complete search history.

(56) References Cited

U.S. PATENT DOCUMENTS

| | | | |
|---|---|---|---|
| 5,605,794 A | 2/1997 | Rust et al. | |
| 5,635,347 A * | 6/1997 | Link et al. | 435/6 |
| 5,650,277 A | 7/1997 | Navot et al. | |
| 5,753,433 A | 5/1998 | Kessler et al. | |
| 5,969,123 A * | 10/1999 | Holtzman | 506/7 |
| 6,004,783 A * | 12/1999 | Ausubel | C12Q 1/683 435/6.14 |
| 6,040,166 A | 3/2000 | Erlich et al. | |
| 6,130,073 A * | 10/2000 | Eggering | 435/91.2 |
| 6,270,965 B1 * | 8/2001 | Kleiber et al. | 435/6 |
| 6,583,112 B1 * | 6/2003 | Fu et al. | 514/2 |
| 6,613,508 B1 * | 9/2003 | Ness et al. | 435/6.12 |
| 7,582,420 B2 * | 9/2009 | Oliphant et al. | 435/6 |
| 2001/0053526 A1 * | 12/2001 | Lipshutz et al. | 435/6 |
| 2002/0142314 A1 * | 10/2002 | Dong et al. | 435/6 |
| 2003/0077575 A1 * | 4/2003 | Stuyver et al. | 435/5 |

FOREIGN PATENT DOCUMENTS

| | | |
|---|---|---|
| CA | 2093647 | 4/1992 |
| DE | 19732086 | 1/1999 |
| EP | 0459533 | 12/1991 |
| EP | 0237362 | 3/1992 |
| EP | 0336731 | 5/1994 |
| EP | 0332435 | 10/1999 |
| WO | WO 90/11369 | 10/1990 |
| WO | WO 92/06216 | 4/1992 |
| WO | WO 94/01447 | 1/1994 |
| WO | WO 03/066897 | 8/2003 |

OTHER PUBLICATIONS

Klepp (Biochemica 2:14-16; 2000).*
Gunneberg et al. (Clin. Chem. 39(10):2157-2162; 1993).*
Canadian Official Action dated Aug. 3, 2011 issued in corresponding Application No. 2,506,654, in English, 2 pages.
Saiki et al., Genetic analysis of amplified DNA with immobilized sequence-specific oligonucleotide probes, Proc. Matl. Acad. Sci. USA, 1989, pp. 6230-6234, vol. 86.
Cotton et al., Mutation detection—a Practical Approach, Oxford University Press, Oxford, 1998, p. 1-198.
Fong et al, Rapid solid-phase immunoassay for detection of a methicillin-resistant *Staphylococcus aureus* using cycling probe technology, J Clin Microbiol, 2000, p. 2525-2529, vol. 38.
Gunneberg et al, Competitive assay to improve the specificity of detection of single-point mutations in alpha 1-antitrypsin deficiency, Clin Chem, 1993, p. 2157-2162, vol. 39(10).
Klepp et al, DNA detection test strip for the rapid detection of digoxigenin- or biotin labeled PCR products, Biochemica, 2000, p. 14-16, vol. 2.
Lay et al, Real-time fluorescence genotyping of factor V Leiden during rapid-cycle PCR, Clin Chem, 1997, p. 2262-2267, vol. 43(12).
Matsubara et al, Detection of single nucleotide substitution by competitive allele-specific short oligonucleotide hybridization (CASSOH) with immunochromatographic strip, Human Mutation, 2003, p. 166-172, vol. 22(2).
Sambrook et al., Molecular Cloning: A Laboratory Manual, vol. 2, Chapter 8, Cold Spring Harbor Press, Cold Spring Harbor, 2001, p. 8.1-8.126.

(Continued)

*Primary Examiner* — Katherine Salmon
(74) *Attorney, Agent, or Firm* — Dentons US LLP

(57) ABSTRACT

DNA amplification and hybridization are successively carried out in a reaction system containing primers for the DNA amplification and hybridization probes, followed by detecting the hybrid in the reaction solution by affinity chromatography, wherein at least one of the primers to be used in the DNA amplification is labeled with a first labeling agent so that the amplified DNA will be labeled with the first labeling agent, a hybridization probe is labeled with a second labeling agent and contained in a reaction solution for effecting the DNA amplification, the base sequence of the hybridization probe is designed not to inhibit the DNA amplification, and a hybrid is detected by affinity chromatography with the use of the first and second labeling agents.

13 Claims, 9 Drawing Sheets

(56) References Cited

OTHER PUBLICATIONS

Notomi et al, Loop-mediated isothermal amplification of DNA, Nucleic Acids Research, 2000, p. e63, 7 pages, vol. 28.
Nozari et al, Discrimination among the transcripts of the allelic human β-globin genes βA, βS and βC using oligodeoxynucleotide hybridization probes, Gene, 1986, p. 23-28, vol. 43.
PCR Methods and Applications, vol. 1, Cold Spring Harbor Laboratory Press, Cold Spring Harbor, 1991, p. 25-33.
DE197321086 published Nov. 21, 2002, abstract only in English, downloaded from Espacenet.com was previously attached to German version of publication, 1 page.
JP04-144700 published May 19, 1992, abstract only in English, downloaded from JP via PAJ was previously attached to 2 Japanese language publication sheets, 3 pages.
JP07-079779 published Mar. 28, 1995, abstract only in English, downloaded from JPO via PAJ, 1 page.
Supplementary European Search Report dated Nov. 21, 2005 in related EP Application No. EP03810655, 1 page.
International Search Report dated Jan. 20, 2004 in related PCT Application No. PCT/JP03/14204, 2 pages.
Saiki et al., Detection of mutations by hybridization with sequence-specific oligonucleotide probes, Published in Cotton et al., Mutation Detection—A Practical Approach, Oxford University Press, 1998, p. 113-129.
Canadian Official Action dated Jul. 25, 2012 issued in related Application No. CA 2,506,654, 2 pages.

* cited by examiner

SEQUENCE LISTING

```
<160> NUMBER OF SEQ ID NOS: 64

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1
cccaaatcct tcctatctct cacag                                         25

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tgctggagtt gagagccagc                                               20
```

```
<210> SEQ ID NO 3
<211> LENGTH: 17
<212> TYPE: DNA
<213> ORGANISM: Artificial Sequence
<220> FEATURE:
<223> OTHER INFORMATION: probe

<400> SEQUENCE: 3
aagctgaaca ggaagaa                                                  17

<210> SEQ ID NO 4
<211> LENGTH: 15
<212> TYPE: DNA
<213> ORGANISM: Artificial Sequence
<220> FEATURE:
<223> OTHER INFORMATION: probe

<400> SEQUENCE: 4
agctgaacag gaaga                                                    15

<210> SEQ ID NO 5
<211> LENGTH: 13
<212> TYPE: DNA
<213> ORGANISM: Artificial Sequence
<220> FEATURE:
<223> OTHER INFORMATION: probe

<400> SEQUENCE: 5
gctgaacagg aag                                                      13

<210> SEQ ID NO 6
<211> LENGTH: 11
<212> TYPE: DNA
<213> ORGANISM: Artificial Sequence
<220> FEATURE:
<223> OTHER INFORMATION: probe

<400> SEQUENCE: 6
ctgaacagga a                                                        11

<210> SEQ ID NO 7
<211> LENGTH: 17
<212> TYPE: DNA
<213> ORGANISM: Artificial Sequence
<220> FEATURE:
<223> OTHER INFORMATION: probe

<400> SEQUENCE: 7
aagctgaaaa ggaagaa                                                  17

<210> SEQ ID NO 8
<211> LENGTH: 15
<212> TYPE: DNA
<213> ORGANISM: Artificial Sequence
<220> FEATURE:
<223> OTHER INFORMATION: probe

<400> SEQUENCE: 8
agctgaaaag gaaga                                                    15

<210> SEQ ID NO 9
<211> LENGTH: 13
<212> TYPE: DNA
<213> ORGANISM: Artificial Sequence
<220> FEATURE:
<223> OTHER INFORMATION: probe
```

-continued

```
<400> SEQUENCE: 9
gctgaaaagg aag                                                    13

<210> SEQ ID NO 10
<211> LENGTH: 11
<212> TYPE: DNA
<213> ORGANISM: Artificial Sequence
<220> FEATURE:
<223> OTHER INFORMATION: probe

<400> SEQUENCE: 10
ctgaaaagga a                                                      11

<210> SEQ ID NO 11
<211> LENGTH: 17
<212> TYPE: DNA
<213> ORGANISM: Artificial Sequence
<220> FEATURE:
<223> OTHER INFORMATION: probe

<400> SEQUENCE: 11
aagctgaaaa ggaagaa                                                17

<210> SEQ ID NO 12
<211> LENGTH: 15
<212> TYPE: DNA
<213> ORGANISM: Artificial Sequence
<220> FEATURE:
<223> OTHER INFORMATION: probe

<400> SEQUENCE: 12
agctgaaaag gaaga                                                  15

<210> SEQ ID NO 13
<211> LENGTH: 13
<212> TYPE: DNA
<213> ORGANISM: Artificial Sequence
<220> FEATURE:
<223> OTHER INFORMATION: probe

<400> SEQUENCE: 13
gctgaaaagg aag                                                    13

<210> SEQ ID NO 14
<211> LENGTH: 11
<212> TYPE: DNA
<213> ORGANISM: Artificial Sequence
<220> FEATURE:
<223> OTHER INFORMATION: probe

<400> SEQUENCE: 14
ctgaaaagga a                                                      11

<210> SEQ ID NO 15
<211> LENGTH: 17
<212> TYPE: DNA
<213> ORGANISM: Artificial Sequence
<220> FEATURE:
<223> OTHER INFORMATION: probe

<400> SEQUENCE: 15
aagctgaaca ggaagaa                                                17

<210> SEQ ID NO 16
<211> LENGTH: 15
```

-continued

```
<212> TYPE: DNA
<213> ORGANISM: Artificial Sequence
<220> FEATURE:
<223> OTHER INFORMATION: probe

<400> SEQUENCE: 16
agctgaacag gaaga                                                  15

<210> SEQ ID NO 17
<211> LENGTH: 13
<212> TYPE: DNA
<213> ORGANISM: Artificial Sequence
<220> FEATURE:
<223> OTHER INFORMATION: probe

<400> SEQUENCE: 17
gctgaacagg aag                                                    13

<210> SEQ ID NO 18
<211> LENGTH: 11
<212> TYPE: DNA
<213> ORGANISM: Artificial Sequence
<220> FEATURE:
<223> OTHER INFORMATION: probe

<400> SEQUENCE: 18
ctgaacagga a                                                      11

<210> SEQ ID NO 19
<211> LENGTH: 12
<212> TYPE: DNA
<213> ORGANISM: Artificial Sequence
<220> FEATURE:
<223> OTHER INFORMATION: probe

<400> SEQUENCE: 19
gctgaacagg aa                                                     12

<210> SEQ ID NO 20
<211> LENGTH: 12
<212> TYPE: DNA
<213> ORGANISM: Artificial Sequence
<220> FEATURE:
<223> OTHER INFORMATION: probe

<400> SEQUENCE: 20
gctgaaaagg aa                                                     12

<210> SEQ ID NO 21
<211> LENGTH: 12
<212> TYPE: DNA
<213> ORGANISM: Artificial Sequence
<220> FEATURE:
<223> OTHER INFORMATION: probe

<400> SEQUENCE: 21
gctgaaaagg aa                                                     12

<210> SEQ ID NO 22
<211> LENGTH: 12
<212> TYPE: DNA
<213> ORGANISM: Artificial Sequence
<220> FEATURE:
<223> OTHER INFORMATION: probe

<400> SEQUENCE: 22
```

```
gctgaacagg aa                                                              12

<210> SEQ ID NO 23
<211> LENGTH: 28
<212> TYPE: DNA
<213> ORGANISM: Artificial Sequence
<220> FEATURE:
<223> OTHER INFORMATION: primer

<400> SEQUENCE: 23 cttttttaatt ctagcaccaa gcaatatc                                            28

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
tccaagtatc tgcacagcat                                                      20

<210> SEQ ID NO 25
<211> LENGTH: 13
<212> TYPE: DNA
<213> ORGANISM: Artificial Sequence
<220> FEATURE:
<223> OTHER INFORMATION: probe

<400> SEQUENCE: 25
gcaatgaaag ttg                                                             13

<210> SEQ ID NO 26
<211> LENGTH: 13
<212> TYPE: DNA
<213> ORGANISM: Artificial Sequence
<220> FEATURE:
<223> OTHER INFORMATION: probe

<400> SEQUENCE: 26
gcaatggaag ttg                                                             13

<210> SEQ ID NO 27
<211> LENGTH: 12
<212> TYPE: DNA
<213> ORGANISM: Artificial Sequence
<220> FEATURE:
<223> OTHER INFORMATION: probe

<400> SEQUENCE: 27
aacttccatt gc                                                              12

<210> SEQ ID NO 28
<211> LENGTH: 12
<212> TYPE: DNA
<213> ORGANISM: Artificial Sequence
<220> FEATURE:
<223> OTHER INFORMATION: probe

<400> SEQUENCE: 28
aactttcatt gc                                                              12

<210> SEQ ID NO 29
<211> LENGTH: 21
<212> TYPE: DNA
<213> ORGANISM: Artificial Sequence
```

```
<220> FEATURE:
<223> OTHER INFORMATION: primer

<400> SEQUENCE: 29
gtctcttggt cctacctaat a                                              21

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
ttagtgaagc tagaacactg                                                20

<210> SEQ ID NO 31
<211> LENGTH: 13
<212> TYPE: DNA
<213> ORGANISM: Artificial Sequence
<220> FEATURE:
<223> OTHER INFORMATION: probe

<400> SEQUENCE: 31
gacgaactgt tca                                                       13

<210> SEQ ID NO 32
<211> LENGTH: 13
<212> TYPE: DNA
<213> ORGANISM: Artificial Sequence
<220> FEATURE:
<223> OTHER INFORMATION: probe

<400> SEQUENCE: 32
gacgaaatgt tca                                                       13

<210> SEQ ID NO 33
<211> LENGTH: 13
<212> TYPE: DNA
<213> ORGANISM: Artificial Sequence
<220> FEATURE:
<223> OTHER INFORMATION: probe

<400> SEQUENCE: 33
gacgaaattg tca                                                       13

<210> SEQ ID NO 34
<211> LENGTH: 13
<212> TYPE: DNA
<213> ORGANISM: Artificial Sequence
<220> FEATURE:
<223> OTHER INFORMATION: probe

<400> SEQUENCE: 34
gacgaactgt tca                                                       13

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
aattacaacc agagcttggc                                                20
```

<210> SEQ ID NO 36
<211> LENGTH: 24
<212> TYPE: DNA
<213> ORGANISM: Artificial Sequence
<220> FEATURE:
<223> OTHER INFORMATION: primer

<400> SEQUENCE: 36
aatatcactt tccataaaag caag                                    24

<210> SEQ ID NO 37
<211> LENGTH: 10
<212> TYPE: DNA
<213> ORGANISM: Artificial Sequence
<220> FEATURE:
<223> OTHER INFORMATION: probe

<400> SEQUENCE: 37
tcccgggaac                                                    10

<210> SEQ ID NO 38
<211> LENGTH: 11
<212> TYPE: DNA
<213> ORGANISM: Artificial Sequence
<220> FEATURE:
<223> OTHER INFORMATION: probe

<400> SEQUENCE: 38
ttcccaggaa c                                                  11

<210> SEQ ID NO 39
<211> LENGTH: 11
<212> TYPE: DNA
<213> ORGANISM: Artificial Sequence
<220> FEATURE:
<223> OTHER INFORMATION: probe

<400> SEQUENCE: 39
ttcccaggaa c                                                  11

<210> SEQ ID NO 40
<211> LENGTH: 10
<212> TYPE: DNA
<213> ORGANISM: Artificial Sequence
<220> FEATURE:
<223> OTHER INFORMATION: probe

<400> SEQUENCE: 40
tcccgggaac                                                    10

<210> SEQ ID NO 41
<211> LENGTH: 25
<212> TYPE: DNA
<213> ORGANISM: Artificial Sequence
<220> FEATURE:
<223> OTHER INFORMATION: primer

<400> SEQUENCE: 41
caaattacag ggtcaactgc tatga                                   25

<210> SEQ ID NO 42
<211> LENGTH: 23
<212> TYPE: DNA
<213> ORGANISM: Artificial Sequence
<220> FEATURE:
<223> OTHER INFORMATION: primer

```
<400> SEQUENCE: 42
agcaggtcct gaacttccag cag                                         23

<210> SEQ ID NO 43
<211> LENGTH: 14
<212> TYPE: DNA
<213> ORGANISM: Artificial Sequence
<220> FEATURE:
<223> OTHER INFORMATION: probe

<400> SEQUENCE: 43
atacactgaa gtga                                                   14

<210> SEQ ID NO 44
<211> LENGTH: 14
<212> TYPE: DNA
<213> ORGANISM: Artificial Sequence
<220> FEATURE:
<223> OTHER INFORMATION: probe

<400> SEQUENCE: 44
atacactaaa gtga                                                   14

<210> SEQ ID NO 45
<211> LENGTH: 15
<212> TYPE: DNA
<213> ORGANISM: Artificial Sequence
<220> FEATURE:
<223> OTHER INFORMATION: probe

<400> SEQUENCE: 45
atacactaaa gtgaa                                                  15

<210> SEQ ID NO 46
<211> LENGTH: 15
<212> TYPE: DNA
<213> ORGANISM: Artificial Sequence
<220> FEATURE:
<223> OTHER INFORMATION: probe

<400> SEQUENCE: 46
atacactgaa gtgaa                                                  15

<210> SEQ ID NO 47
<211> LENGTH: 22
<212> TYPE: DNA
<213> ORGANISM: Artificial Sequence
<220> FEATURE:
<223> OTHER INFORMATION: primer

<400> SEQUENCE: 47
attatgcctg gcaccattaa ag                                          22

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
cattcacagt agcttaccca                                             20

<210> SEQ ID NO 49
```

```
<211> LENGTH: 15
<212> TYPE: DNA
<213> ORGANISM: Artificial Sequence
<220> FEATURE:
<223> OTHER INFORMATION: probe

<400> SEQUENCE: 49
aatatcattg gtgtt                                                    15

<210> SEQ ID NO 50
<211> LENGTH: 14
<212> TYPE: DNA
<213> ORGANISM: Artificial Sequence
<220> FEATURE:
<223> OTHER INFORMATION: probe

<400> SEQUENCE: 50
tatcatcttt ggtg                                                     14

<210> SEQ ID NO 51
<211> LENGTH: 24
<212> TYPE: DNA
<213> ORGANISM: Artificial Sequence
<220> FEATURE:
<223> OTHER INFORMATION: primer

<400> SEQUENCE: 51
ccaggaatct cctcagcttt gtgt                                          24

<210> SEQ ID NO 52
<211> LENGTH: 21
<212> TYPE: DNA
<213> ORGANISM: Artificial Sequence
<220> FEATURE:
<223> OTHER INFORMATION: primer

<400> SEQUENCE: 52
agcctccttt ggttagcaag g                                             21

<210> SEQ ID NO 53
<211> LENGTH: 15
<212> TYPE: DNA
<213> ORGANISM: Artificial Sequence
<220> FEATURE:
<223> OTHER INFORMATION: probe

<400> SEQUENCE: 53
tatatctatc ctatg                                                    15

<210> SEQ ID NO 54
<211> LENGTH: 13
<212> TYPE: DNA
<213> ORGANISM: Artificial Sequence
<220> FEATURE:
<223> OTHER INFORMATION: probe

<400> SEQUENCE: 54
gtatatccta tgg                                                      13

<210> SEQ ID NO 55
<211> LENGTH: 22
<212> TYPE: DNA
<213> ORGANISM: Artificial Sequence
<220> FEATURE:
<223> OTHER INFORMATION: primer

<400> SEQUENCE: 55
```

-continued ctttcagcat gattttgaag tc                                            22

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
gggagtggaa tacagagtgg                                               20

<210> SEQ ID NO 57
<211> LENGTH: 13
<212> TYPE: DNA
<213> ORGANISM: Artificial Sequence
<220> FEATURE:
<223> OTHER INFORMATION: probe

<400> SEQUENCE: 57
agaatcccca gga                                                      13

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
gatgaatgta gcacgcattc                                               20

<210> SEQ ID NO 59
<211> LENGTH: 19
<212> TYPE: DNA
<213> ORGANISM: Artificial Sequence
<220> FEATURE:
<223> OTHER INFORMATION: primer

<400> SEQUENCE: 59
tcttgtgagc tggtctgaa                                                19

<210> SEQ ID NO 60
<211> LENGTH: 15
<212> TYPE: DNA
<213> ORGANISM: Artificial Sequence
<220> FEATURE:
<223> OTHER INFORMATION: probe

<400> SEQUENCE: 60
acagcaaggg aaaat                                                    15

<210> SEQ ID NO 61
<211> LENGTH: 25
<212> TYPE: DNA
<213> ORGANISM: Artificial Sequence
<220> FEATURE:
<223> OTHER INFORMATION: primer

<400> SEQUENCE: 61
ggttccaagt agaatattta aagaa                                         25

<210> SEQ ID NO 62
<211> LENGTH: 22
<212> TYPE: DNA

```
<213> ORGANISM: Artificial Sequence
<220> FEATURE:
<223> OTHER INFORMATION: primer

<400> SEQUENCE: 62
ccattattta gccaggagac ct                                              22

<210> SEQ ID NO 63
<211> LENGTH: 12
<212> TYPE: DNA
<213> ORGANISM: Artificial Sequence
<220> FEATURE:
<223> OTHER INFORMATION: probe

<400> SEQUENCE: 63
acaggcaagg aa                                                         12

<210> SEQ ID NO 64
<211> LENGTH: 12
<212> TYPE: DNA
<213> ORGANISM: Artificial Sequence
<220> FEATURE:
<223> OTHER INFORMATION: probe

<400> SEQUENCE: 64
acaggcgagg aa                                                         12
```

METHOD OF DETECTING GENE MUTATION

CROSS REFERENCE TO RELATED APPLICATIONS

This application claims the benefit of U.S. non-provisional application Ser. No. 10/533,750, filed May 4, 2005 (incorporated herein by reference in its entirety), which was a national stage entry of PCT/JP03/14204, filed Nov. 7, 2003, which in turn claims priority to JP 2002-323419, filed Nov. 7, 2002. This application also claims the benefit of priority to JP 2002-323419.

INCORPORATION-BY-REFERENCE OF SEQUENCE LISTING

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

TECHNICAL FIELD

The present invention relates to a method of detecting a base sequence, and more particularly to a method of detecting a base sequence containing a mutation site such as a point mutation, thereby detecting a gene mutation.

BACKGROUND ART

There exist a number of gene polymorphisms on the genome, which have been considered to be deeply associated with susceptibility to diseases, individual variations in drug metabolism, and the like. The detection of the gene polymorphism is indispensable for so-called tailor-made medicine and becomes one of the most important subjects on the clinical applications of genomic science. Among others, much interest is lately focused on SNP (single nucleotide polymorphism; gene polymorphism caused by substitution of a single base) as a marker of the gene polymorphism, on which huge research funds have been spent on a global basis. On the other hand, data on gene mutations associated with various genetic diseases has been accumulated into databases by virtue of progress on molecular genetics research. Accordingly, it has become reality to make the diagnosis of genetic diseases or the prediction of clinical categories by screening for known gene mutations already found to be pathogenic on the basis on these databases. In particular, a gene mutation that occurs with high frequency within a certain population or interracially is of great diagnostic value.

The gene polymorphism and gene mutation include, for example, a base substitution, deletion, insertion, and variations in the number of repetitive sequences, and among them, a point mutation caused by substitution of a single base makes up the overwhelming majority. A method of simply and quickly detecting a point mutation is indispensable for applying the outcomes of human genome research to clinical purposes.

Until now, a variety of methods have been devised for detecting a point mutation (see Cotton R G H. Mutation Detection. pp. 1-198, Oxford University Press, Oxford, 1997). Typical methods include the allele specific oligonucleotide hybridization (ASO) method, allele specific amplification method, restriction enzyme digestion method, ligase chain reaction, and minisequencing method. These methods require complicated procedures including hybridization or electrophoresis after DNA amplification. On the other hand, the TaqMan method, invader assay, DNA microarray (DNA chip) assay, TOF-MASS method with the use of a mass spectrometer, and the like, which have been recently developed for promoting the human genome analysis and research, are suited to deal with a large number of samples. However, these methods require high-priced, specialized instruments and cannot be easily performed at clinical laboratories. Alternatively, the SSCP method, chemical cleavage method, and DHPLC method are widely used for screening of gene mutations, and are highly effective for broad screening of unknown gene mutations; but are inadequate to reliable detection of a known mutation. In addition, the detection of a point mutation by the use of the sequencing method requires complicated procedures and high expenses, and is of undeniably too much quality for the detection of a known mutation. At present, all of these methods described above involve special examinations performed at gene research laboratories and find a great difficulty in quick performance in clinical settings (or at bedside).

Probes used in the ASO method has been conventionally 15 to 25 mer (see Saiki R K, Erlich H A. Detection of mutations by hybridization with sequence-specific oligonucleotide probes. In: Mutation Detection: A Practical Approach. pp. 113-129, IRL Press, Oxford, 1998). Moreover, it is known that the specificity of a labeled probe for hybridization is enhanced using an oligonucleotide that competes with the probe (see Nozari G. Rahbar S, Wallace R B. Discrimination among the transcripts of the allelic human β-globin genes $β^A$, $β^S$ and $β^C$ using oligodeoxynucleotide hybridization probes. Gene 43: 23-28, 1986).

DISCLOSURE OF THE INVENTION

An object of the present invention is to provide a method of simply and quickly detecting a gene mutation.

The present inventors have used to achieve the present invention the findings that the use of certain primers and probes under a certain condition enables both amplification and hybridization of nucleic acids in one reaction system, and also enables a easy detection of a hybrid formed by the hybridization.

The present invention provides the following:

(1) A method of detecting a base sequence, comprising the steps of: amplifying DNA containing a target base sequence to be detected having a mutation site using DNA polymerase; hybridizing the amplified DNA to a hybridization probe having a base sequence complementary to the target base sequence to be detected; and detecting a hybrid formed by the hybridization, wherein at least one of primers to be used in the DNA amplification is labeled with a first labeling agent so that the amplified DNA will be labeled with the first labeling agent, the hybridization probe is labeled with a second labeling agent and contained in a reaction solution for effecting the DNA amplification, the base sequence of the hybridization probe is designed not to inhibit the DNA amplification, and the hybrid is detected by affinity chromatography with the use of the first and second labeling agents.

(2) The method according to item (1), wherein the mutation site is a point mutation, and the reaction solution for effecting the DNA amplification further contains an unlabeled oligonucleotide having a base sequence different in a single base at the position of the point mutation from the base sequence of the labeled hybridization probe, in an amount sufficient to enhance the specificity of hybridization of the amplified DNA to the hybridization probe.

(3) The method according to item (1) or (2), wherein the DNA amplification is carried out by PCR.

(4) A kit comprising: primers for amplifying DNA containing a target base sequence to be detected having a mutation site using DNA polymerase; a hybridization probe having a base sequence complementary to the target base sequence to be detected; and a test strip for affinity chromatography, wherein at least one of the primers to be used in the DNA amplification is labeled with a first labeling agent so that the amplified DNA will be labeled with the first labeling agent, the hybridization probe is labeled with a second labeling agent, the base sequence of the hybridization probe is designed not to inhibit the DNA amplification, and the test strip allows of detection of a hybrid of the amplified DNA and the hybridization probe with the use of the first and second labeling agents.

(5) The kit according to item (4), wherein the mutation site is a point mutation and the kit further comprises an unlabeled oligonucleotide having a base sequence different in a single base at the position of the point mutation from the base sequence of the labeled hybridization probe.

(6) The kit according to item (4) or (5), wherein the primers are primers for PCR.

BEST MODE FOR CARRYING OUT THE INVENTION

Figure 1:
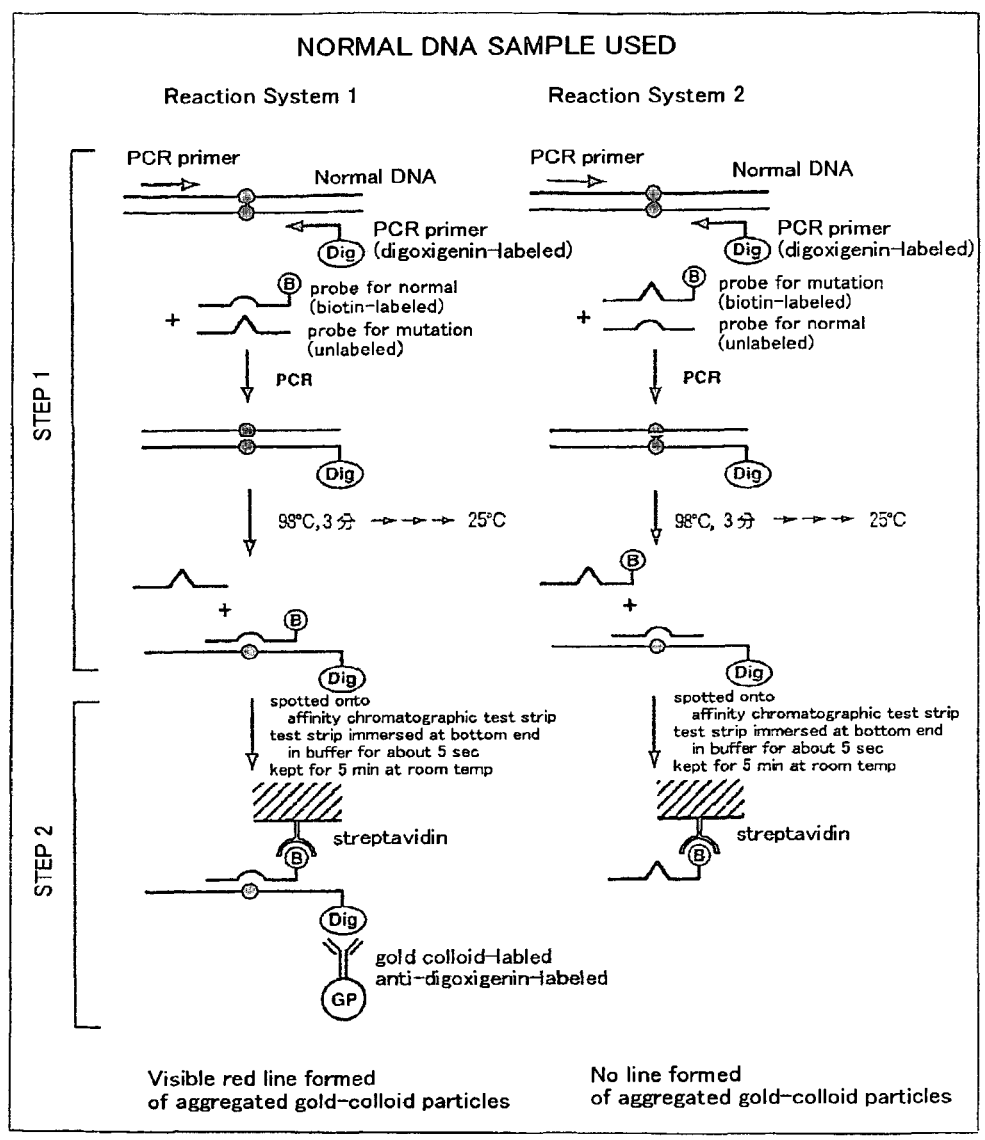
FIG. 1 shows the principle of the detection method according to the present invention (when normal DNA is used as a sample).

<1> Detection Method of the Present Invention

In the present invention, there is provided a method of detecting a base sequence, which comprises the steps of: amplifying DNA containing a target base sequence to be detected having a mutation site using DNA polymerase; hybridizing the amplified DNA to a hybridization probe having a base sequence complementary to the target base sequence to be detected; and detecting a hybrid formed by the hybridization; characterized in that at least one of primers to be used in the DNA amplification is labeled with a first labeling agent so that the amplified DNA will be labeled with the first labeling agent, the hybridization probe is labeled with a second labeling agent and contained in a reaction solution for effecting the DNA amplification, the base sequence of the hybridization probe is designed not to inhibit the DNA amplification, and the hybrid is detected by affinity chromatography with the use of the first and second labeling agents. Hereinafter, each of the steps will be described.

(1) DNA Amplification

The DNA amplification is carried out, if using DNA polymerase, without any particular limitation. Any amplification methods comprising the step of synthesizing DNA with the use of DNA polymerase can be employed. Examples of the DNA amplification method include PCR, TMA, NASBA, and LAMP methods.

The synthesis of DNA with DNA polymerase requires primers. The primers are designed by a method known in the art depending on an amplification method to be used and a target base sequence to be detected. In the present invention, at least one of primers to be used in DNA amplification is labeled with a first labeling agent so that the amplified DNA will be labeled with the first labeling agent.

For example, when DNA amplification is effected by the PCR method, a pair of primers are used and at least one thereof is labeled so that the amplified DNA can be labeled. Alternatively, a primer that functions at the stage of DNA synthesis in DNA amplification by the NASBA and TMA methods or at least one of inner primers in DNA amplification by the LAMP method is labeled, thereby allowing the labeling of the amplified DNA.

The labeling of primers is carried out so as not to inhibit DNA synthesis reaction. Such labeling can be carried out according to a method known in the art, and a primer is usually labeled at its 5' end.

A labeling agent to be used in the labeling may be those to which a corresponding substance can be biospecifically bound. A pair of the labeling agent and the substance biospecifically bound thereto includes an antigen and an antibody, an enzyme and an inhibitor, a sugar chain and lectin, a hormone and a receptor, and a metal-binding protein and a metal element. Specifically, a pair of digoxigenin and an anti-digoxigenin antibody and a pair of biotin and streptavidin may be used. In these pairs, either of the two may be given as a labeling agent. However, the smaller molecular weight partner is generally used as a labeling agent.

Primers and DNA amplification conditions to be used are appropriately adjusted on the basis of type of an amplification method and a target base sequence to be detected. For example, see: Molecular Cloning: A Laboratory Manual (3rd ed.), Volume 2, Chapter 8, pp. 8.1-8.126, Cold Spring Harbor Laboratory Press, Cold Spring Harbor, 2001 on the PCR method; PCR Methods and Applications, 1, 25-33 (1991) on the NASBA method; and Nucleic Acids Research, Vol. 28, No. 12, pp. i-vii (2000) on the LAMP method.

Test DNA that functions as a template in DNA amplification can be prepared from a test sample by a conventional method.

The target base sequence to be detected is appropriately selected depending on the type of an amplification method so that the target base sequence having a mutation site can be specifically amplified. In general, the mutation site contained in the target base sequence to be detected is known as a site of gene mutation or gene polymorphism. The mutation of the site may be a point mutation, an insertion mutation or a deletion mutation.

Common examples of the gene mutation and gene polymorphism to be analyzed by the detection method of the present invention include, but not limited to: g727t mutation observed with high frequency in Japanese patients with glycogen storage disease type Ia; a985g mutation (Lys329Glu mutation) observed with high frequency in Caucasian patients with middle-chain acyl-CoA dehydrogenase deficiency; g1691t mutation (Ser564Ile mutation) of GLDC gene observed with high frequency in Finnish patients with hyperglycinemia; gene polymorphism (CYP2C19*2, g681a) in drug metabolizing enzyme gene CYP2C19; gene polymorphism (E487K) of an aldehyde dehydrogenase 2 determining individual variations in alcohol metabolism; deltaF508 deletion mutation in the gene of cystic fibrosis transmembrane regulator protein; 1277insTATC insertion mutation in HEXA gene associated with Tay-Sachs disease; 5382insC insertion mutation in BRCA1 gene associated with breast cancer; 6174delT deletion mutation in BRCA2 gene associated with breast cancer; and G1691A point mutation in Blood Coagulation Factor V gene associated with thrombosis.

Glycogen storage disease type Ia is a congenital disorder of carbohydrate metabolism, inherited in an autosomal recessive manner, caused by deficiency of glucose-6-phosphatase in the glycogen metabolic pathway, and leads to an excess accumulation of glycogen mainly in the liver. Patients with glycogen storage disease type Ia are found to have hypoglycemia, hepatomegaly, short statue, renal damage, hyperlipidemia, hyperuricemia, or the like. Mutation g727t in the gene of this enzyme is a highly frequent mutation making up approximately 90% of pathogenic mutations in Japanese cases, and generates aberrant splicing of its mRNA. Although the diagnosis of this disease has been usually performed until very recently by measuring enzyme activity of liver tissues, the emergence of genetic diagnosis has eliminated the need of liver biopsy. The number of carriers having this mutation in Japanese population is one in about 200 people.

Non-ketotic hyperglycinemia is a congenital disorder of amino acid metabolism (autosomal recessive inheritance) caused by deficiency of an enzyme of the glycine cleavage system, and exhibits severe neurological symptoms including neonatal convulsion during neonatal period. Mutation g1691t in GLDC gene of the enzymes in the glycine cleavage system is observed with high frequency (approximately 70% of mutated genes) in Finnish patients. This mutation causes an amino acid substitution of Ser564Ile.

Middle-chain acyl-CoA dehydrogenase deficiency is a congenital disorder of organic acid metabolism (autosomal recessive inheritance) caused by deficiency of the enzyme (middle-chain acyl-CoA dehydrogenase, MCAD) playing a key role in fatty acid P oxidation pathway, and brings about hypoglycemia and consciousness disturbance at fasting and infection. It is known that middle-chain acyl-CoA dehydrogenase deficiency is often misdiagnosed as sudden infant death syndrome or acute encephalopathy (Reye syndrome). Mutation a985g in the gene of this enzyme is a highly frequent mutation making up approximately 90% of pathogenic mutations in Caucasian cases, and produces an amino acid substitution of Lys329Glu. Moreover, carriers having this gene mutation are found with high frequency in Caucasian population (one in 40 people in the U.K.). In U.S.A. and European countries, the genetic diagnosis of detecting this a985g mutation is widely used for diagnosis of this disease.

CYP2C19 gene plays a key role in the metabolism of omeprazole (inhibitor of gastric acid secretion) or the like. CYP2C19*2, a SNP in the gene, shows 681A>G mutation in exon 5, leading to aberrant splicing, and thus finally decreases in the metabolic activity to this drug. An individual having such a polymorphism (poor metabolizer) needs a decreased amount of the drug to be administrated to the subject. Therefore, it is clinically advantageous to determine the genotype of a patient before the medication. This gene polymorphism is found in approximately 23% of the gene in Japanese population.

The gene polymorphism (Glu487Lys) of aldehyde dehydrogenase 2 is a SNP, observed largely in oriental population, to determine individual variations in alcohol metabolism. Because the enzyme having the gene polymorphism is less active to slow down the metabolism of acetaldehyde generated from alcohol, an individual having this polymorphism shows a constitutional "low tolerance for alcohol". Approximately 30% in Japanese population have a heterozygote of this gene polymorphism and approximately 5% have a homozygote thereof.

(2) Hybridization

The hybridization of the amplified DNA to a hybridization probe having a base sequence complementary to the target base sequence to be detected may be carried out in the same manner as general hybridization except that a particular hybridization probe is used.

The hybridization probe used in the present invention is labeled with a second labeling agent and contained in a reaction solution for effecting the DNA amplification, and the base sequence of the hybridization probe is designed not to inhibit the DNA amplification.

The second labeling agent is defined as described in the first labeling agent; provided that the substance used for it must be different from the first labeling agent. The labeling of the hybridization probe can be carried out by a method known in the art so as not to inhibit the hybridization. The labeling of the hybridization probe is preferably carried out at its 3' end. This is because such labeling prevents the oligonucleotide chain from being extended during the DNA amplification reaction. If the chain is extended in length, the Tm value thereof is increased and thus hybridization may occur even though there are mismatches.

The design of the base sequence of the hybridization probe so as not to inhibit the DNA amplification can be generally selected by adjusting the chain length or the like of the hybridization probe so that the hybridization of the hybridization probe will not occur under the DNA amplification condition.

The hybridization probe used in the present invention has a base sequence designed so as not to inhibit the DNA amplification, and can be thus previously contained in a reaction solution for effecting the DNA amplification. Therefore, the reaction solution after the DNA amplification is completed is placed directly under such a condition that the amplified DNA can be hybridized to the hybridization probe, thereby allowing the hybridization thereof.

The chain length of the hybridization probe and the condition of hybridization thereof are appropriately selected depending on a method used in the DNA amplification. In DNA amplification with the use of DNA polymerase, because the amplification is effected under a temperature condition suitable to for the DNA polymerase exhibit its activity, the chain length is selected so that the hybridization will not occur at this temperature. In addition, the temperature at which the hybridization occurs is not particularly limited as long as DNA amplification is not inhibited, but is preferably selected so that the generated hybrid may not be dissociated even at room temperature.

A specific condition under which the base sequence of the probe does not inhibit the DNA amplification includes a condition that the Tm of the probe is designed to be 25 to 40° C. (preferably 30 to 35° C.) lower than the Tm of primers.

For example, with consideration given to general conditions of the PCR method, the probe should be typically 10-mers to 13-mers. This is much shorter than 15-mer to 25-mer probes (see the above-mentioned non-patent reference 2) that have been conventionally used as a probe for allele specific oligonucleotide hybridization. In the context of that longer probes have been extensively used heretofore, there has been the theory that a sequence of at least about the 15th power of 4 is required for constructing a probe having specificity by combinations of four different bases in the whole genome sequence (3 billion base pairs). However, this holds true for the case where hybridization is directed toward the whole genome sequences. When hybridization is directed to a PCR-amplified DNA fragment having several hundreds of bases, such length or specificity is not considered necessary for probes that the specificity of hybridization is sufficiently maintained with the former probe as shown above.

When using the detection method of the present invention for the detection of any gene mutation or polymorphism, the hybridization probe is required to be adjusted to an optimum chain length. The optimum length can be determined by a standard experimentation, as described in Examples below. Because an extremely short length of a probe is usually used in the detection method of the present invention, formation of a diagnostic line is found to dramatically vary depending on the length variations by a single base. When the emergence of false positive or weak positive reaction is observed, it is preferred that a probe having a shorter or longer length than that of the probe designed based on its Tm value may be constructed to choose the most suitable one. In this respect, because a probe having a normal base sequence and a probe having a mutant base sequence are different in Tm value due to the base substitution even though they have the same chain length, each optimum chain length should be designed independently.

It is preferred to design the base sequence of the hybridization probe so that the mutation site will be positioned in approximately middle of the base sequence.

Hybridization is usually carried out by increasing a temperature until double-stranded DNA is denatured, followed by gradually lowering the temperature. Thus, the hybridization can be carried out by only a procedure of changing the temperature of a reaction solution in which DNA amplification is completed, without the need of any other procedures. In the case of using a programmable thermal cycler in DNA amplification, a temperature condition for hybridization can be programmed in addition to a temperature condition requisite to the DNA amplification, thereby effecting the amplification and the hybridization as a series of reactions, after a sample is loaded in the thermal cycler.

The use of a short length of the probe designed as described above provides the following three advantages: 1) the difference in Tm values between the case where there is a mismatch of a single base and the case where there is no mismatch can be rendered larger than that of a longer length of a probe, and thus the specificity of the probe can be relatively increased; 2) the hybridization temperature of the probe can be given as low as 25° C. in the detection method of the present invention, although conventionally 37 to 65° C., and thus a subsequent series of procedures can be carried out at room temperature; and 3) a short length of the probe has a reduced Tm value and does not hybridize during PCR reaction, and thus the probe does not affect the PCR reaction even though it is previously mixed in the PCR reaction solution. This probe enables the procedures PCR→heat denaturation→hybridization to be carried out as a series of reactions, without performance of additional procedures such as the addition of a reagent during the reactions. These advantages can be similarly obtained in other DNA amplification methods with the use of an extension reaction by DNA polymerase, as in the PCR method.

(3) Detection of Hybrid

A hybrid formed by the hybridization has both the first labeling agent and the second labeling agent. The hybrid is detected by affinity chromatography with the use of the first and second labeling agents.

The affinity chromatography can be carried out with a test strip constructed for this purpose. The detection of a hybrid by affinity chromatography with the use of two different labeling agents can be carried out according to a method known in the art, and a test strip used in this method can be constructed according to a general method.

An example of such a test strip is constructed so that a hybrid will be reacted with a substance which is capable to be specifically bound to the first labeling agent and is coupled with a labeling agent (e.g., gold colloid) to become visible when accumulated; and transferred onto a chromatography support on which a substance capable to be specifically bound to the second labeling agent is immobilized, to allow of the observation of the visible labeling agent when accumulated on that immobilization site. Such a test strip itself has been also used so far in a method of simply detecting a certain gene (J. Clin. Microbiol. 38: 2525-2529, 2000).

Hereinafter, an illustration will be provided in a specific case where the first labeling agent is digoxigenin, the second labeling agent is biotin, and the labeling agent that is visible when accumulated is gold colloid. The following sites are placed in the order named in the migration direction of a chromatography solvent (generally, a buffer solution): an immersion site that is immersed in a chromatography solvent to provide the chromatography solvent to the strip of the chromatography support; a complex-carrying site that has a pad carrying an anti-digoxigenin antibody conjugated with gold colloid (a complex) in a manner that this antibody can be released into the chromatography solvent; a sample-applying site to which the reaction solution containing a hybrid is applied; a streptavidin-immobilized site on which a band of streptavidin is immobilized perpendicularly to the migration direction of the chromatography solvent; an antibody-immobilized site on which an antibody against the anti-digoxigenin antibody is immobilized; and an absorption site that has a pad absorbing the chromatography solvent.

This test strip is used as described below. After the reaction solution containing the hybrid is applied to the sample-applying site and the immersion site is immersed in the chromatography solvent, the test strip is removed from the chromatography solvent and left to stand. When the chromatography solvent migrates through the chromatography support by capillary action and reaches the complex-carrying site, from which the chromatography solvent containing the complex will migrate forward. When this chromatography solvent reaches the sample-applied site, the digoxigenin of the hybrid in the applied reaction solution will bind to the anti-digoxigenin antibody of the complex to form the hybrid having the gold colloid, which further migrates forward through the chromatography support by the chromatography solvent. When the hybrid reaches the streptavidin-immobilized site, this hybrid will be accumulated on the streptavidin-immobilized site through the binding of biotin and streptavidin; consequently a visible signal shall be seen when the hybrid is present. The complex that has passed through the streptavidin-immobilized site is accumulated on the antibody-immobilized site to generate a visible signal showing that the chromatogram has proceeded normally. The chromatography solvent further migrating will be absorbed and held in the absorption site.

In the detection method of the present invention, if the mutation site is a point mutation, preferably, the reaction solution for effecting DNA amplification further contains, along with the hybridization probe, an unlabeled oligonucleotide (hereinafter, also referred to as a "competing probe") having a base sequence different in a single base at the position of the point mutation from the base sequence of the labeled hybridization probe, in an amount sufficient to enhance the specificity of the hybridization of the amplified DNA to the labeled hybridization probe.

The competing probe is designed in the same way as the hybridization probe except that it differs from the hybridization probe in a single base at the position of the point mutation. The length of the competing probe may be different from that of the hybridization probe.

The amount of the competing probe sufficient to enhance the specificity of the hybridization of the amplified DNA to the labeled hybridization probe varies depending on conditions such as the target base sequence to be detected and the base sequence of the hybridization probe, whereas in principle, the competing probe may be usually contained in the range from an equal amount to 5-fold amount (molar ratio) with respect to the amount of the hybridization probe. Nevertheless, when positive reaction is significantly reduced, the omission of the competing probe, if it is confirmed not to cause false positives, may sometimes produce the best result. Because the formation of a diagnostic line is significantly affected by the chain length of the hybridization probe and the presence or absence of the competing probe, an optimum reaction condition will be relatively easily found.

The specificity of the hybridization probe can be enhanced and non-specific hybridization can be suppressed by adding an unlabeled competing oligonucleotide in the hybridization.

In the detection method of the present invention, different labeling agents may be used for labeling a hybridization probe for detecting a normal base sequence and a hybridization probe for detecting a mutant base sequence, to integrate two reaction systems for detecting a normal base sequence and for detecting a mutant base sequence into one reaction system. That is, the hybridization probes for detecting a normal base sequence and for detecting a mutant base sequence can be differently labeled and mixed together in the ratio of 1:1 to integrate the reaction systems into one while these hybridization probes are allowed to compete with each other. After the reaction, using the complexes of substances which are capable of specifically binding to the labeling agents, respectively, and a labeling agent that becomes visible when accumulated, affinity chromatography is carried out to determine a genotype.

The detection method of the present invention has the following advantages: (1) versatility: the method is based on allele specific oligonucleotide hybridization that has been widely used as a detection method for a long time, and therefore adaptable to detection of a wide range of base sequence mutations such as an insertion mutation, a substitution mutation, and a point mutation; (2) rapidity: the determination of a genotype can be carried out within 10 minutes after the amplification and hybridization reactions have been completed in a thermal cycler, and the use of a capillary-type PCR amplification device in the nucleic acid amplification also enables all steps to be completed within 1 hour, if a DNA sample is ready; and (3) simplicity: after PCR reaction, a genotype can be macroscopically determined, thereby eliminating the need for an instrument such as a gel electrophoresis device or a fluorescence detector. A thermal cycler for effecting PCR reaction is a general-purpose instrument for clinical examination, for example, an examination for infectious diseases, and has been already placed in many hospitals. Moreover, the reaction procedure is simple without the need for special technical skills. The above-described advantages can be also obtained when nucleic acid reactions (TMA, NASBA, LAMP, etc.) other than PCR are used.

Figure 2:
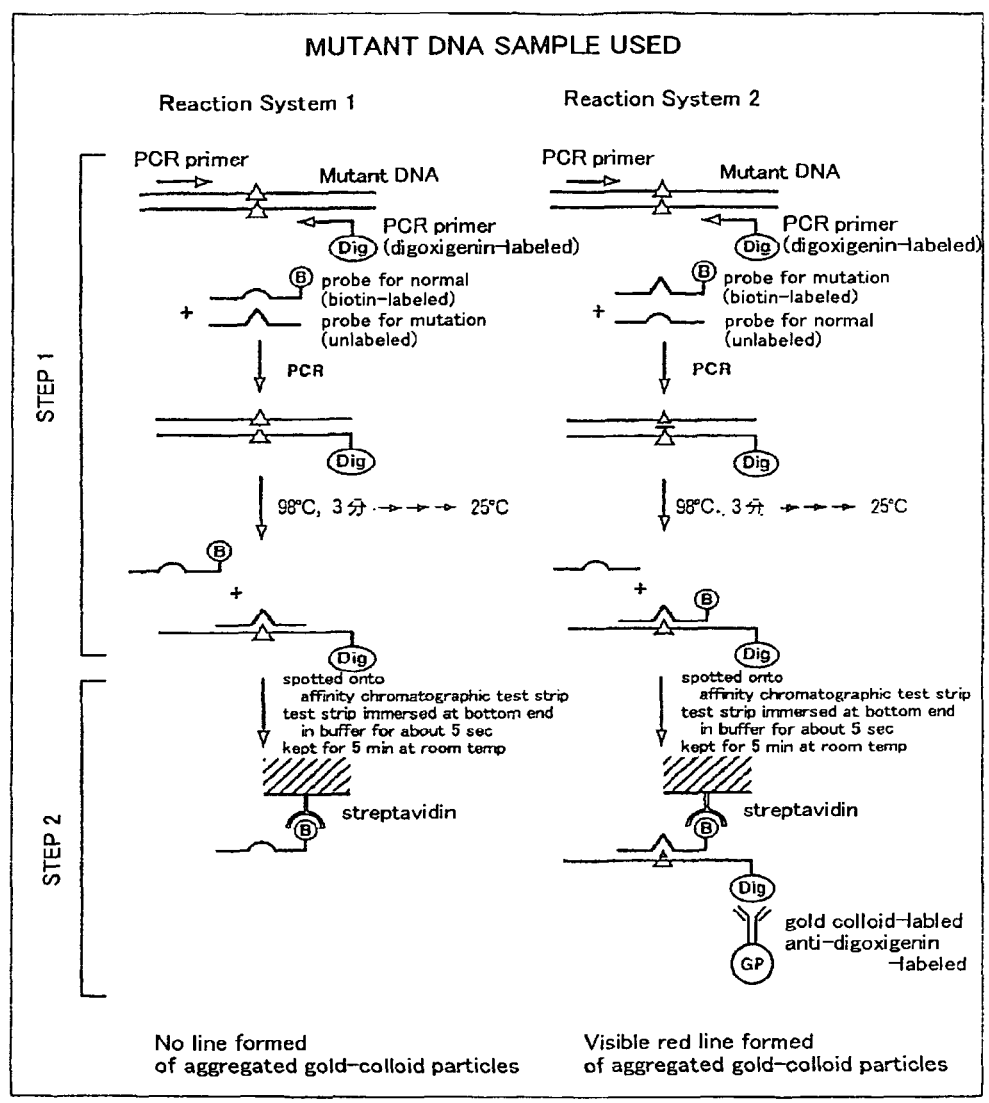
FIG. 2 shows the principle of the detection method according to the present invention (when mutant DNA is used as a sample).
Figure 3:
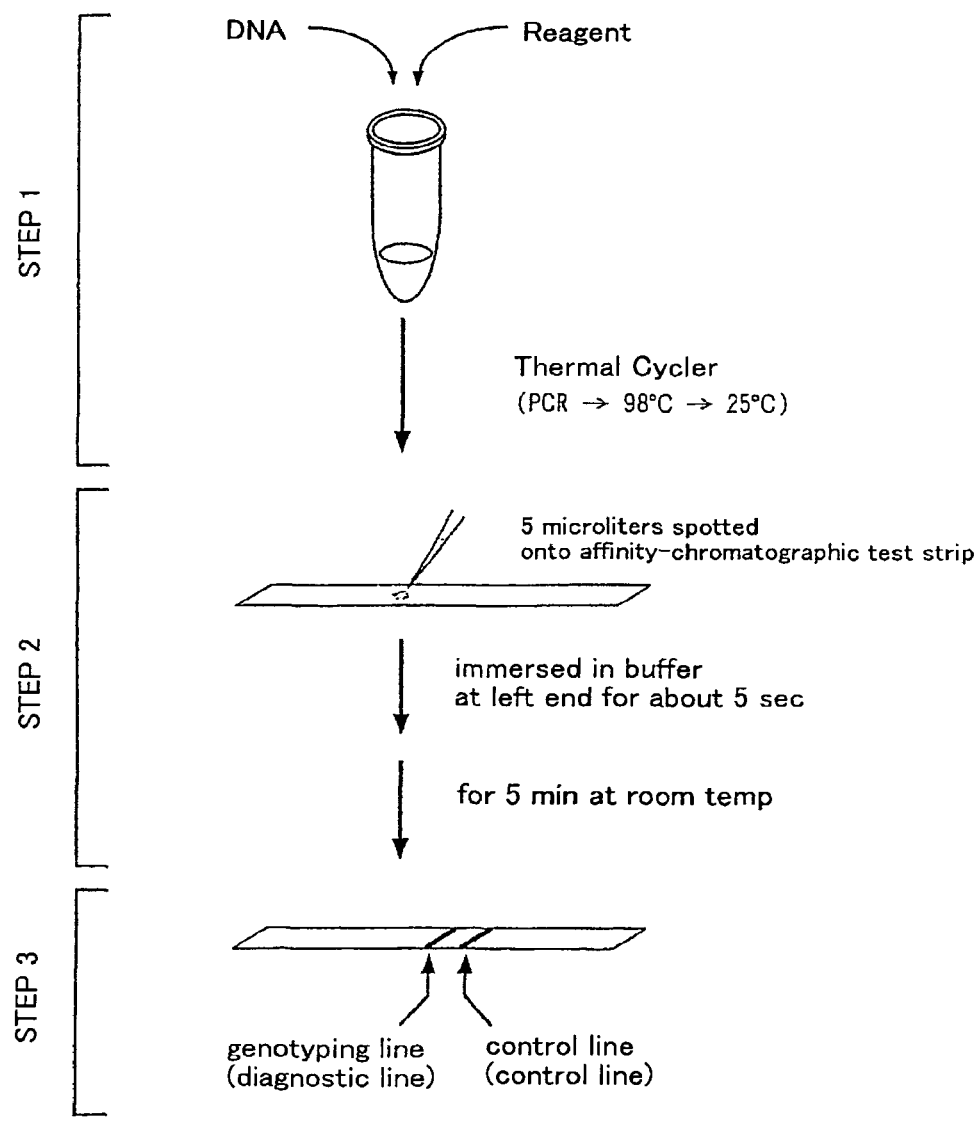
FIG. 3 shows an example of procedures used in the detection method according to the present invention.

The principle of the detection method of the present invention will be more fully illustrated in the case using PCR with reference to FIGS. 1 to 3.

FIG. 1 shows a reaction with the use of normal DNA as a sample. Reaction system 1 is a system to which is added a hybridization probe for detecting a normal base sequence and reaction system 2 is a system to which is added a hybridization probe for detecting a mutant base sequence. In this figure, the black circle represents a normal base, the black triangle represents a mutant base, Dig represents a digoxigenin label, B represents a biotin label, and GP represents a gold particle.

At first, a gene site having a point mutation (the target base sequence to be detected) is amplified by PCR. One primer of the PCR primer pair used in this case has been previously labeled at its 5' end with digoxigenin. In a PCR reaction solution, two oligonucleotides (hybridization probe and competing probe) have been mixed with typical components. In this combination of the oligonucleotides, there exist two combinations for detecting a normal base sequence and for detecting a mutant base sequence. In the combination for detecting a normal base sequence, one is an oligonucleotide (normal probe) having a normal base sequence with the point mutation site located in the middle portion thereof and labeled with biotin at its 3' end; and the other is an unlabeled competing oligonucleotide (mutant probe) having a mutant base sequence with the point mutation site located in the middle portion thereof. In the combination for detecting a mutant base sequence, one is an oligonucleotide (mutant probe) having a mutant base sequence with the point mutation site located in the middle portion thereof and labeled with biotin at its 3' end and the other is an unlabeled competing oligonucleotide (normal probe) having a normal base sequence with the point mutation site located in the middle portion thereof. Any of these oligonucleotides are designed to be a reverse strand relative to the PCR primer labeled with digoxigenin.

The composition of the PCR reaction solution is, for example, 50 to 100 ng of sample DNA, 10 mM Tris-HCl (pH 8.3), 50 mM KCl, 1.5 mM $MgCl_2$, 250 µM each dNTPs, 1 µM PCR forward primer (labeled with digoxigenin at its 5' end), 1 µM PCR reverse primer, 600 nM hybridization probe (labeled with biotin at its 3' end), 3 µM unlabeled competing oligonucleotide, and 1.25 U Taq DNA polymerase, and the amount of the PCR reaction solution is 20 µl. The PCR condition is: for example, heating at 94° C. for 2 minutes; 35 cycles of 98° C. for 10 seconds, 55° C. for 30 seconds, and 72° C. for 30 seconds; followed by 72° C. for 3 minutes; 98° C. for 3 minutes; 65° C. for 1 minute; 55° C. for 1 minute; 45° C. for 1 minute; 35° C. for 1 minute; and 25° C. for 1 minute. In this process after the cycle reactions are repeated, a PCR product labeled with digoxigenin is hybridized with oligonucleotide having a base sequence completely complementary to the base sequence of the PCR product. For example, when oligonucleotides for detecting a normal base sequence is used with the DNA having a normal base sequence in combination, a PCR product labeled with digoxigenin and an oligonucleotide labeled with biotin form a hybrid (FIG. 1, reaction system 1). An aliquot (5 µl) of this solution is spotted onto the sample-applying site in a test strip of affinity chromatography, such as DNA detection test strip (Roche, #1-965-484), on which streptavidin is immobilized and in which an anti-digoxigenin antibody labeled with gold colloid is held in a manner that the antibody can migrate, and the bottom end of the test strip is immersed in a buffer for 5 seconds. As the strip is left to stand at room temperature for 5 minutes while the buffer is developed, the anti-digoxigenin antibody labeled with gold colloid binds to the hybrid of the PCR product labeled with digoxigenin and the oligonucleotide labeled with biotin. This hybrid is further captured by streptavidin immobilized on the test strip to form a red line that can be macroscopically observed. On the other hand, when oligonucleotides for detecting a mutant base sequence is used with the DNA having a normal base sequence in combination, a PCR product labeled with digoxigenin and an unlabeled oligonucleotide form a hybrid. After this solution is spotted to the sample-applying site of the test strip and subjected to a development with a buffer, an anti-digoxigenin antibody labeled with gold colloid binds to the hybrid of the PCR product labeled with digoxigenin and the unlabeled oligonucleotide. However, because this hybrid is not captured by streptavidin on the test strip, a red line is not formed (FIG. 1, reaction system 2). As described above, macroscopically observing a formation of red line in each of the two different reaction systems will make it possible to make a determination of the genotype of DNA given as a sample. The principle of the reaction of DNA having a mutant base sequence is the same as above (FIG. 2).

The operation procedures in this aspect are shown in FIG. 3. At first, a DNA as a sample is mixed with a reaction reagent in a PCR tube and heated/cooled with a thermal cycler according to the program to effect the DNA amplification and the formation of a hybrid (Step 1). An aliquot (5 µl) of the reaction solution is spotted to the sample-applying site of the test strip and the bottom end of the test strip is immersed in a buffer, followed by standing at room temperature (Step 2). After 5 minutes, the diagnosis is conducted on the basis of the presence or absence of the diagnostic line to determine a genotype (Step 3). Whether the affinity chromatography is normally completed or not can be confirmed by examining the presence or absence of a control line.

The detection method of the present invention is a method capable of quickly and simply determining the presence or absence of a gene mutation with accuracy and without the use of a special device, and is suitable to conduct a genetic test in a hospital outpatient clinic or at bed side. That is, the detection method allows of a genetic diagnosis as a Point of Care. More particularly, the gene polymorphism of drug-metabolizing enzymes including CYP2C19 will be decided, which made it possible to determine on the spot whether or not a certain drug is suitable for a patient and to assist the adjustment of the dosage. In this case, an important advantage is that a test result can be obtained in a short time.

<2> Kit of the Present Invention

The kit of the present invention comprises: primers for amplifying DNA containing a target base sequence to be detected having a mutation site using DNA polymerase; a hybridization probe having a base sequence complementary to the target base sequence to be detected; and a test strip for affinity chromatography;

characterized in that at least one of the primers to be used in the DNA amplification is labeled with a first labeling agent so that the amplified DNA will be labeled with the first labeling agent, the hybridization probe is labeled with a second labeling agent, the base sequence of the hybridization probe is designed not to inhibit the DNA amplification, and the test strip allows of detection of a hybrid of the amplified DNA and the hybridization probe with the use of the first and second labeling agents. The kit of the present invention can be used for carrying out the detection method of the present invention.

The primers, the hybridization probe, and the test strip for affinity chromatography are as described above in the detection method of the present invention.

If the mutation site is a point mutation, preferably, the kit of the present invention further comprises an unlabeled oligonucleotide (competing probe) having a base sequence different in a single base at the position of the point mutation from the base sequence of the labeled hybridization probe. This oligonucleotide is as described above in the detection method of the present invention.

EXAMPLES

The present invention will be described in detail with reference to the following examples, which are only intended to concretely illustrate the present invention, but not intend to restrict the scope of the present invention in any way.

Example 1

Detection of Mutation g727t in Glycogenosis Type Ia (1) Reaction System and Experimental Procedure For detecting g727t mutation in glycogenosis Type Ia, primers listed in Table 1 were prepared on the basis of known base sequences around the mutation site.

TABLE 1

Primers and probes for detection of g727t mutation in glycogenosis type Ia

PCR forward primer (G6P-E5-1F-Dig):
5'-Dig-CCCAAATCCTTCCTATCTCTCACAG-3'  (SEQ ID NO: 1)

PCR reverse primer (G6P-E5-1R(20)):
5'-TGCTGGAGTTGAGAGCCAGC-3'  (SEQ ID NO: 2)

For examining the effect of chain lengths of probes, oligonucleotides listed in Table 2 were prepared as hybridization probes and competing probes.

TABLE 2

(I) Biotin-labeled oligonucleotide for detection of normal base sequence:

| 17 mer: | 5'-AAGCTGAACAGGAAGAA-Biotin-3' | (SEQ ID NO: 3) |
| 15 mer: | 5'-AGCTGAACAGGAAGA-Biotin-3' | (SEQ ID NO: 4) |
| 13 mer: | 5'-GCTGAACAGGAAG-Biotin-3' | (SEQ ID NO: 5) |
| 11 mer: | 5'-CTGAACAGGAA-Biotin-3' | (SEQ ID NO: 6) |

(II) Unlabeled competing oligonucleotide for detection of normal base sequence:

| 17 mer: | 5'-AAGCTGAAAAGGAAGAA-3' | (SEQ ID NO: 7) |
| 15 mer: | 5'-AGCTGAAAAGGAAGA-3' | (SEQ ID NO: 8) |
| 13 mer: | 5'-GCTGAAAAGGAAG-3' | (SEQ ID NO: 9) |
| 11 mer: | 5'-CTGAAAAGGAA-3' | (SEQ ID NO: 10) |

(III) Biotin-labeled oligonucleotide for detection of mutant base sequence:

| 17 mer: | 5'-AAGCTGAAAAGGAAGAA-Biotin-3' | (SEQ ID NO: 11) |
| 15 mer: | 5'-AGCTGAAAAGGAAGA-Biotin-3' | (SEQ ID NO: 12) |
| 13 mer: | 5'-GCTGAAAAGGAAG-Biotin-3' | (SEQ ID NO: 13) |
| 11 mer: | 5'-CTGAAAAGGAA-Biotin-3' | (SEQ ID NO: 14) |

(IV) Unlabeled competing oligonucleotide for detection of mutant base sequence:

| 17 mer: | 5'-AAGCTGAACAGGAAGAA-3' | (SEQ ID NO: 15) |
| 15 mer: | 5'-AGCTGAACAGGAAGA-3' | (SEQ ID NO: 16) |
| 13 mer: | 5'-GCTGAACAGGAAG-3' | (SEQ ID NO: 17) |
| 11 mer: | 5'-CTGAACAGGAA-3' | (SEQ ID NO: 18) |

The PCR reaction solution consists of 50-100 ng of sample DNA, 10 mM Tris-HCl (pH 8.3), 50 mM KCl, 1.5 mM MgCl$_2$, 250 µM each dNTPs, 1 µM of PCR forward primer, 1 µM of PCR reverse primer (labeled with digoxigenin at the 5' end), 600 nM of hybridization probe (labeled with biotin at the 3' end), unlabeled competing oligonucleotide at a predetermined concentration, and 1.25 U Taq DNA polymerase in a final volume of 20 µl. The PCR was carried out by heating at 94° C. for 2 minutes and repeating 35 times a cycle of 98° C. for 10 seconds, 55° C. for 30 seconds and 72° C. for 30 seconds, followed by 72° C. for 3 minutes, 98° C. for 3 minutes, 65° C. for 1 minute, 55° C. for 1 minute, 45° C. for 1 minute, 35° C. for 1 minute, and 25° C. for 1 minute.

An aliquot (5 µl) of the solution was spotted on a sample-applying site of a test strip (DNA Detection Test Strip, Roche Co., Ltd., #1-965-484, an affinity chromatographic test strip on which streptavidin is immobilized and in which an anti-digoxigenin antibody labeled with gold colloid is held in a movable manner) and then the bottom end of the strip was immersed in a buffer for 5 seconds. Then the test strip was left to stand for 5 minutes at room temperature to allow the buffer to move through the strip. After the keeping, the presence or absence of a genotype diagnostic line was macroscopically determined.

(2) Examination of Competition with Unlabeled Oligonucleotide

Figure 4:
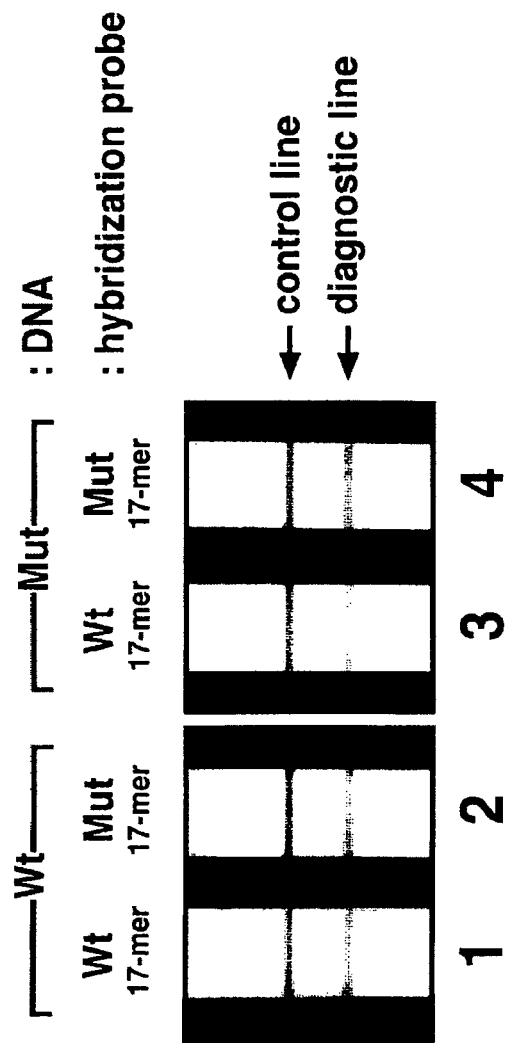
FIG. 4 shows the result of detection (chromatogram images) in the case of using a 17-mer hybridization probe.

The labeled hybridization probe used was of 17 mers and the detection was then carried out without the addition of a competing probe in a reaction solution. The DNA samples used were a homozygote for g727 allele (normal DNA) and a homozygote for t727 allele (mutant DNA), and the hybridization probes used were those for the detection of a normal base sequence and for the detection of a mutant base sequence. The results are shown in FIG. 4. In this figure, the indications "Wt" and "Mut" with respect to "DNA" represent the normal DNA and the mutant DNA, respectively, while the indications "Wt" and "Mut" with respect to "hybridization probe" represent the hybridization probes for the detection of a normal base sequence and for the detection of a mutant base sequence, respectively (the same holds for FIG. 5 to FIG. 7 described below).

In any of the combinations tested, a false positive red reaction line was recognized. Thus, the genotyping was unsuccessful (FIG. 4, lanes 1-4).

Figure 5:
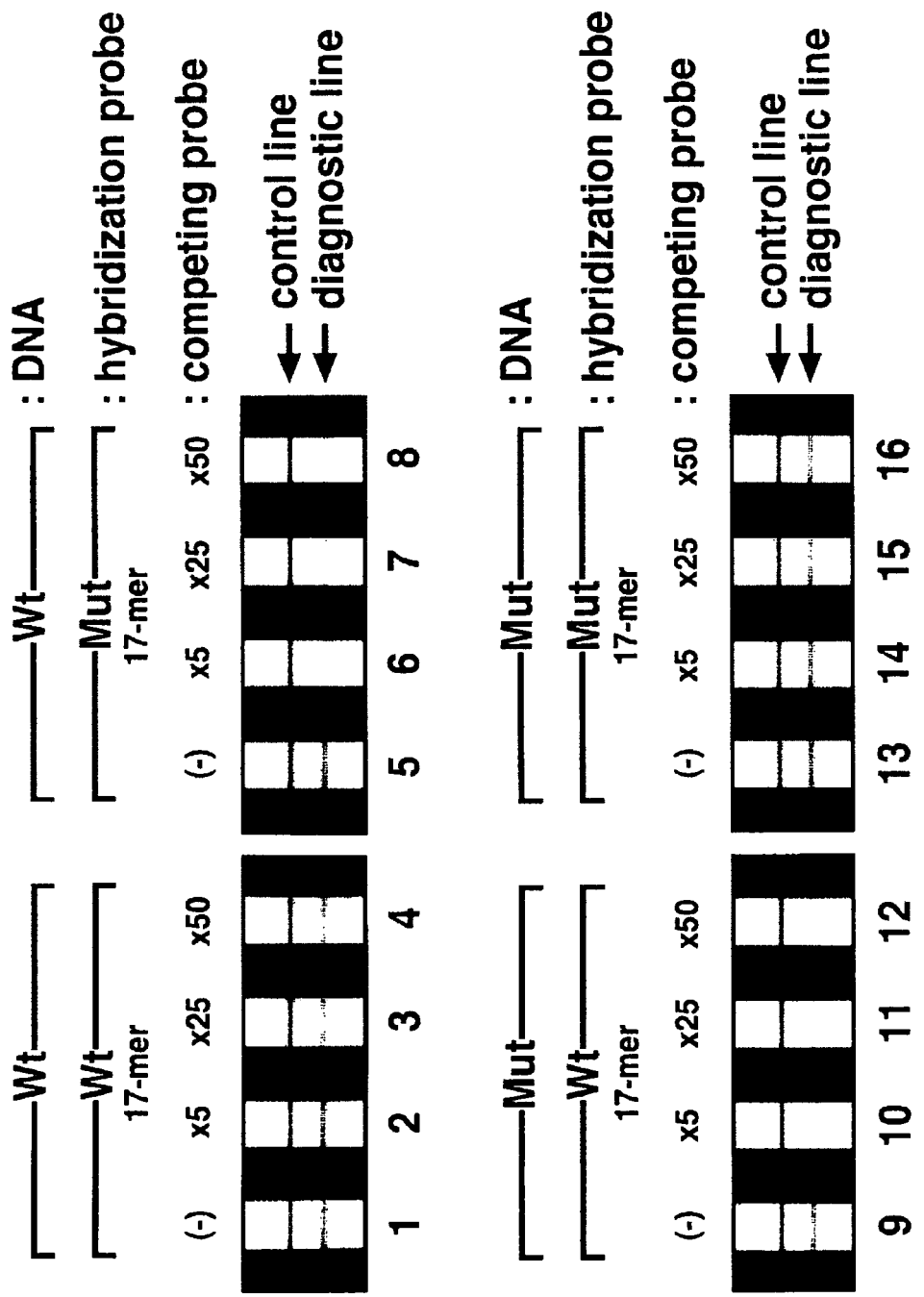
FIG. 5 shows the result of detection (chromatogram images) in the case of using a 17-mer hybridization probe and adding a competing probe.

A similar experiment was carried out by adding 5-50 times more amount (molar concentrations) of the competing probe (17 mers) than that of the hybridization probe to the reaction solution. The results are shown in FIG. 5.

The addition of the competing probe resulted in a substantial decrease in false positive reactions. In other words, only very slight red reaction lines were observed in reaction systems of probes for detecting a mutant base sequences with a normal DNA (FIG. 5, lanes 6-8) and in reaction systems of probes for detecting a normal base sequences with a mutant DNA (FIG. 5, lanes 10-12). No difference was found in inhibitory effect on a false positive reaction in any amounts of the competing probe added, and even the addition of 50-fold amount could not completely inhibit the false positive reaction. On the contrary, it was found that the addition of 25-50 fold amounts inhibited normal positive reactions so that the reaction lines would tend to become fairly pale (FIG. 5, lanes 3, 4, 15, and 16).

(3) Examination of Chain Length of Hybridization Probe

The hybridization probes and competing probes used in this study were of 17 mers, 15 mers, 13 mers, and 11 mers. The amount of the competing probes added to the reaction solution was fixed to 30 times more than that of the hybridization probe. The results are shown in FIG. 6.

Figure 6:
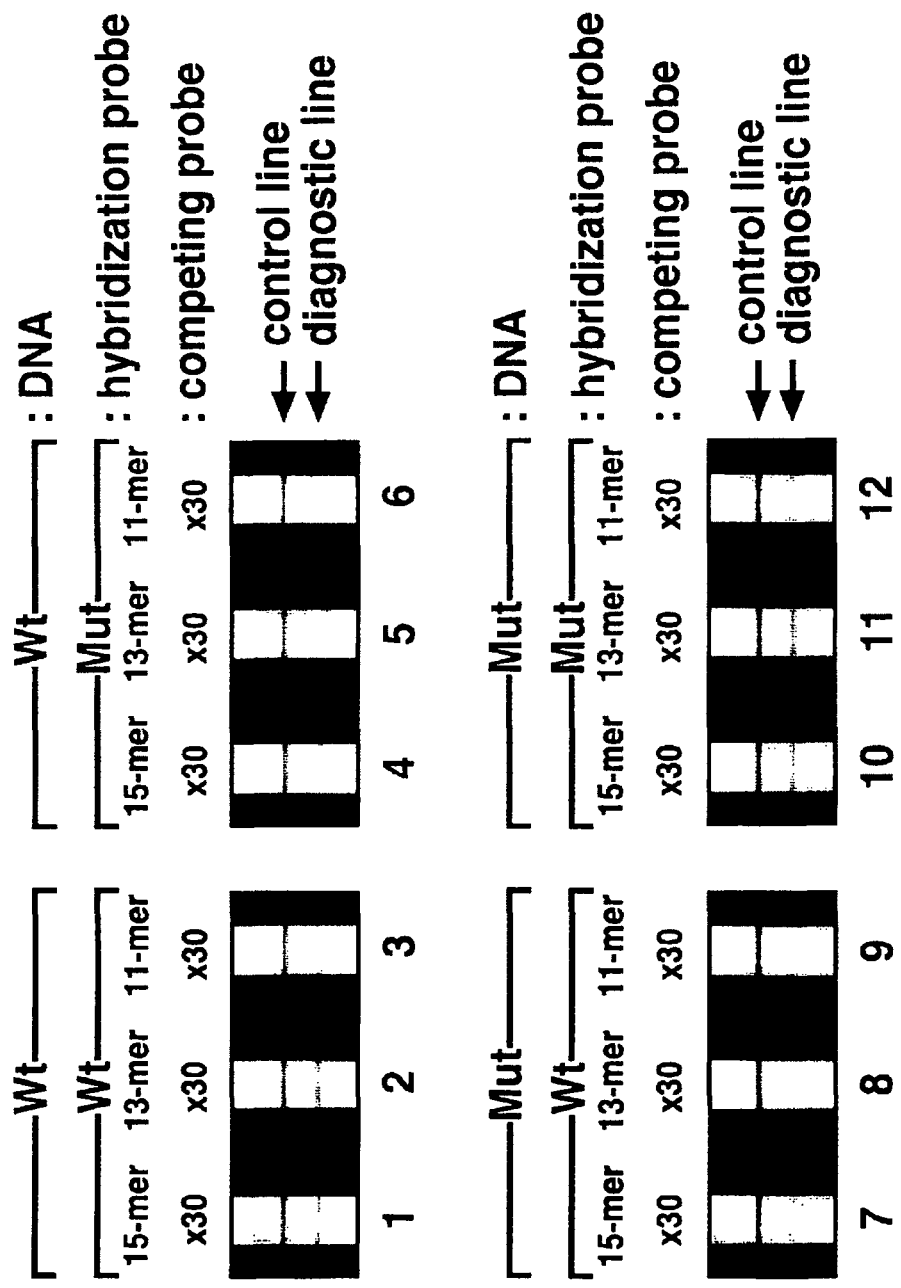
FIG. 6 shows the result of detection (chromatogram images) in the case of using hybridization probes of various lengths and adding a competing probe.

In the reaction system of probes for detecting a mutant base sequence to a normal DNA, a faint false positive line appeared in case of 15 mers (FIG. 6, lane 4), but not appeared in cases of 13 mers and 11 mers (FIG. 6, lanes 5 and 6). In the reaction system of probes for detecting a normal base sequence to a mutant DNA, no false positive appeared in any cases of 15 mers, 13 mers and 11 mers (FIG. 6, lanes 7 to 9). Nevertheless, it was found that the normal positive reactions tended to become decreased in case of 11 mer (FIG. 6, lanes 3 to 12).

In consideration of the results of examinations as described above, using the hybridization and competing probes of 12 mers in chain length (Table 3) with the five-fold amount of the competing probe added, the detection was carried out in a similar manner for samples of normal DNA (homozygote of g727 allele), carrier's DNA (heterozygote of g727 allele and t727 allele), and patient's DNA (homozygote of t727 allele). The results are shown in FIG. 7.

Figure 7:
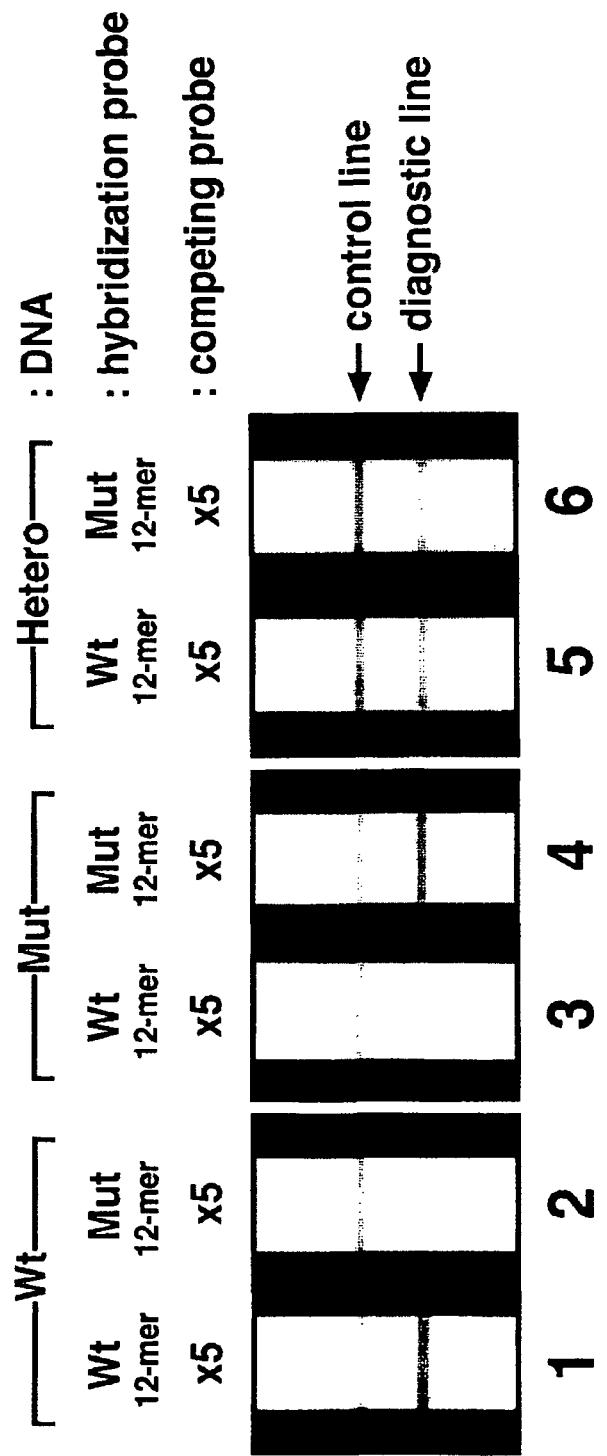
FIG. 7 shows the result of detection (chromatogram images) in the case of using a 12-mer hybridization probe and adding a competing probe.

The results obtained completely corresponds to the genotype with distinct positive reaction lines observed (FIG. 7, lanes 1 and 4 and lanes 5 and 6). On the contrary, no false positive reaction were found (lanes 2 and 3).

TABLE 3

Biotin-labeled oligonucleotide for detection
of normal base sequence
(GSD727-ASO-W12-Bio):

5'-GCTGAACAGGAA-Biotin-3'      (SEQ ID NO: 19)

TABLE 3-continued

Unlabeled competing oligonucleotide for detection
of normal base sequence
(GSD727-ASO-M12):

5'-GCTGAAAAGGAA-3'            (SEQ ID NO: 20)

Biotin-labeled oligonucleotide for detection
of mutant base sequence
(GSD727-ASO-M12-Bio):

5'-GCTGAAAAGGAA-Biotin-3'     (SEQ ID NO: 21)

Unlabeled competing oligonucleotide for
detection of mutant base sequence
(GSD727-ASO-W12):

5'-GCTGAACAGGAA-3'            (SEQ ID NO: 22)

Example 2

Detection of Mutation a985g of Middle-Chain Acyl-CoA Dehydrogenase Deficiency, Mutation g1691t of GLDC Gene in Hyperglycinemia, Mutation g681a of Drug-Metabolizing Enzyme Gene CYP2C19, and Point Mutation of Glu487Lys of Aldehyde Dehydrogenase 2 Polymorphism The detection method of the present invention was carried out to detect a point mutation, including mutation a985g of middle-chain acyl-CoA dehydrogenase deficiency, mutation g1691t of GLDC gene in hyperglycinemia, mutation g681a of drug-metabolizing enzyme gene CYP2C19, and point mutation of Glu487Lys of aldehyde dehydrogenase 2 polymorphism.

The PCR primers for amplifying base sequences containing the respective point mutation sites were adjusted in chain length so as to carry out PCR reactions with setting of an annealing temperature of 55° C. In addition, the hybridization probes were designed to have Tm values in the range of 35 to 40° C. As a result, the chain lengths thereof were 10 mers to 15 mers. The base sequences of primers, hybridization probes, and competing probes are listed in Table 4.

TABLE 4

(I) Primers and probes for detection of a985g mutation of
gene of middle-chain acyl-CoA dehydrogenase deficiency
PCR forward primer (Dig-MCAD-F1):

5'-Dig-CTTTTTAATTCTAGCACCAAGCAATATC-3'  (SEQ ID NO: 23)

PCR reverse primer (Dig-MCAD-R1):

5'-Dig-TCCAAGTATCTGCACAGCAT-3'          (SEQ ID NO: 24)

Biotin-labeled oligonucleotide for detection of normal base
sequence (Bio-MCAD985-W13):

5'-GCAATGAAAGTTG-Biotin-3'              (SEQ ID NO: 25)

Unlabeled competing oligonucleotide for detection of normal
base sequence (MCAD985-M13):

5'-GCAATGGAAGTTG-3'                     (SEQ ID NO: 26)

Biotin-labeled oligonucleotide for detection of mutant base
sequence (Bio-MCAD985-M12):

5'-AACTTCCATTGC-Biotin-3'               (SEQ ID NO: 27)

TABLE 4-continued

Unlabeled competing oligonucleotide for detection of mutant base sequence (MCAD985-W12):

5'-AACTTTCATTGC-3'  (SEQ ID NO: 28)

(II) Primers and probes for detection of g1691t mutation of GLDC gene
PCR forward primer (Dig-GLDC-F):

5'-Dig-GTCTCTTGGTCCTACCTAATA-3'  (SEQ ID NO: 29)

PCR reverse primer (GLDC-R):

5'-TTAGTGAAGCTAGAACACTG-3'  (SEQ ID NO: 30)

Biotin-labeled oligonucleotide for detection of normal base sequence (Bio-S5641-W13):

5'-GACCAACTGTTCA-Biotin-3'  (SEQ ID NO: 31)

Unlabeled competing oligonucleotide for detection of normal base sequence (S5641-M13):

'-GACGAAATGTTCA-3'  (SEQ ID NO: 32)

Biotin-labeled oligonucleotide for detection of mutant base sequence (Bio-S5641-M):

5'-GACGAAATGTTCA-Biotin-3'  (SEQ ID NO: 33)

Unlabeled competing oligonucleotide for detection of mutant base sequence (S5641-W):

5'-GACGAACTGTTCA-3'  (SEQ ID NO: 34)

(III) Primers and probes for detection of gene polymorphism CYP2C19*2 of CYP2C19 gene
PCR forward primer (CYP2C19-P1):

5'-AATTACAACCAGAGCTTGGC-3'  (SEQ ID NO: 35)

PCR reverse primer (Dig-CYP2C19-P2):

5'-Dig-AATATCACTTTCCATAAAAGCAAG-3'  (SEQ ID NO: 36)

Biotin-labeled oligonucleotide for detection of normal base sequence (Bio-CYP2C19-W):

5'-TCCCGGGAAC-Biotin-3'  (SEQ ID NO: 37)

Unlabeled competing oligonucleotide for detection of normal base sequence (CYP2C19-M):

5'-TTCCCAGGAAC-3'  (SEQ ID NO: 38)

Biotin-labeled oligonucleotide for detection of polymorphic base sequence (Bio-CYP2C19-M):

5'-TTCCCAGGAAC-Biotin-3'  (SEQ ID NO: 39)

Unlabeled competing oligonucleotide for detection of polymorphic base sequence (CYP2C19-W):

5'-TCCCGGGAAC-3'  (SEQ ID NO: 40)

(IV) Primers and probes for detection of polymorphism of aldehyde dehydrogenase 2 gene
PCR forward primer (Dig-ALDH2-AF):

5'-Dig-CAAATTACAGGGTCAACTGCTATGA-3'  (SEQ ID NO: 41)

PCR reverse primer (Dig-ALDH2-AR2):

5'-Dig-AGCAGGTCCTGAACTTCCAGCAG-3'  (SEQ ID NO: 42)

Biotin-labeled oligonucleotide for detection of normal base sequence (Bio-ALDH2-PW2):

5'-Biotin-ATACACTGAAGTGA-Biotin-3'  (SEQ ID NO: 43)

TABLE 4-continued

Unlabeled competing oligonucleotide for detection of normal base sequence (ALDH2-CM2):

5'-ATACACTAAAGTGA-3'                    (SEQ ID NO: 44)

Biotin-labeled oligonucleotide for detection of polymorphic base sequence (Bio-ALDH2-PM2):

5'-Biotin-ATACACTAAAGTGAA-Biotin-3'     (SEQ ID NO: 45)

Unlabeled competing oligonucleotide for detection of polymorphic base sequence (ALDH2-CW2):

5'-ATACACTGAAGTGAA-3'                   (SEQ ID NO: 46)

All the PCR conditions or conditions including the concentrations of probes were the same as those of Example 1 in any cases of detecting the mutations described above, except that the above primers and probes must be used.

Figure 8:
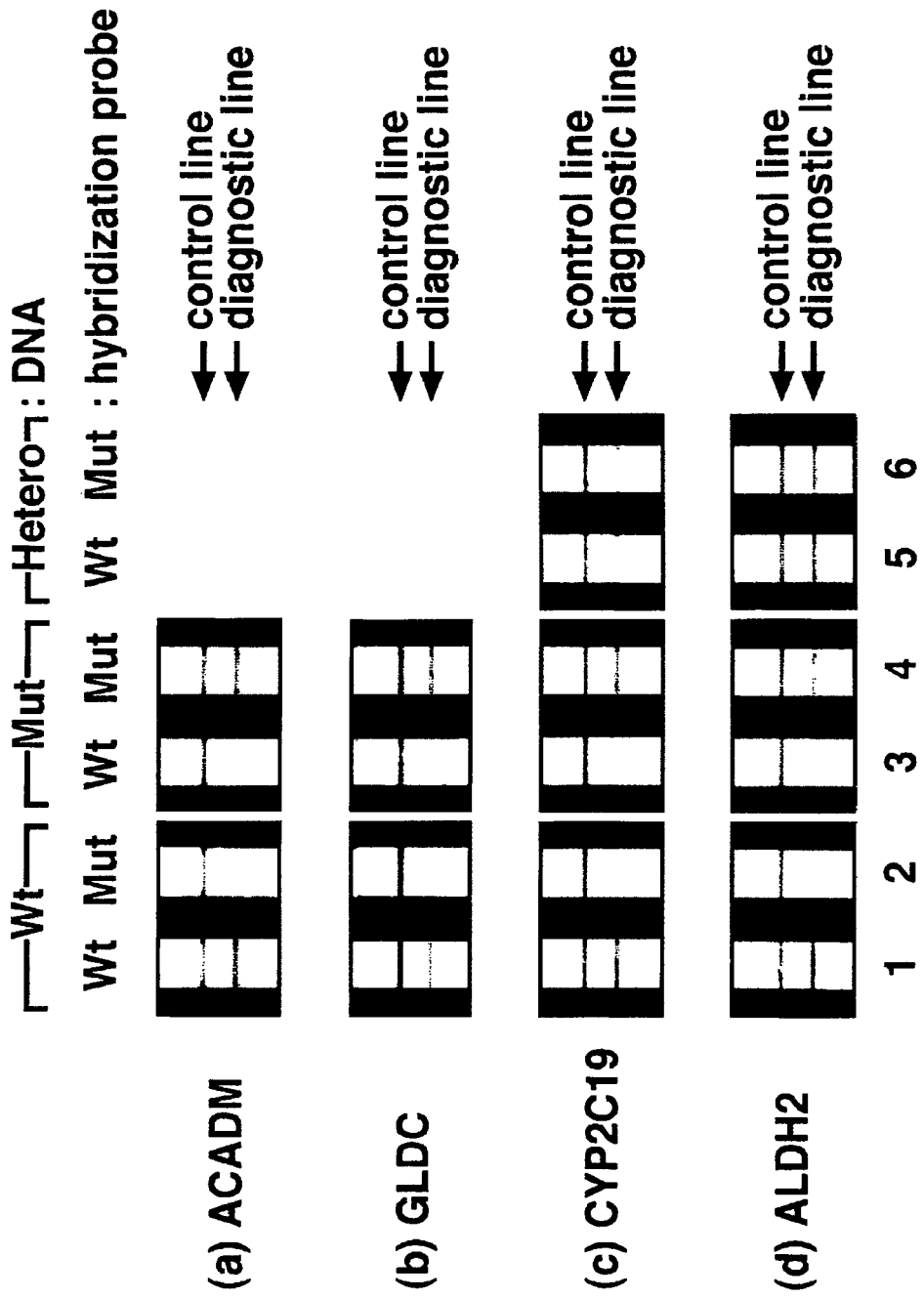
FIG. 8 shows the result of the detection (chromatogram images) of a variety of mutations.

The detections, as carried out under these conditions, showed the correct determination of genotypes in all of the detection systems (FIGS. 8, a, b, c, and d). In the detection of Glu487Lys of aldehyde dehydrogenase 2 gene polymorphism, the reaction line obtained was weak in the reaction system for detecting a mutant base sequence. However, when unlabeled competing oligonucleotide was not mixed in this reaction system, the formation of distinct reaction line was observed. In each of the reactions, no false positive was observed.

The determination of genotype was completed within 10 minutes after the completion of reaction in the thermal cycler. Even at least two years after the test strip was dried without any treatment and stored at room temperature, a macroscopic determination thereof was possible.

The above-mentioned results show that the detection method of the invention allows of the simple and quick detection of each mutation or polymorphism of the five genes to determine the genotype of sample DNA, even though the design of primers and hybridization probes and competing probes, and the reaction conditions are required to be adjusted slightly for and depending on the respective gene mutations. Therefore, it is concluded that the detection method of the present invention can be used for many purposes.

Example 3

Detection of Delta F508 Deletion Mutation in Cystic Fibrosis Transmembrane Regulator Protein Gene, 1277insTATC Insertion Mutation in HEXA Gene of Tay-Sachs Disease, 5382insC Insertion Mutation in BRCA1 Gene of Breast Cancer, 6174delT Deletion Mutation in BRCA2 Gene of Breast Cancer, and G1691A Point Mutation in Blood Coagulation Factor V Gene of Thrombosis The detection method of the present invention was carried out to detect a mutation, including deltaF508 deletion mutation in the gene of cystic fibrosis transmembrane regulator protein; 1277insTATC insertion mutation in HEXA gene of Tay-Sachs disease; 5382insC insertion mutation in BRCA1 gene of breast cancer; 6174delT deletion mutation in BRCA2 gene of breast cancer; and G1691A point mutation in Blood Coagulation Factor V gene of thrombosis.

The PCR primers for amplifying base sequences containing the respective mutation sites were adjusted in chain length so as to carry out PCR reactions with setting of an annealing temperature of 55° C. In addition, the hybridization probes were designed to have Tm values in the range of 35 to 40° C. As a result, the chain lengths thereof were 10 mers to 15 mers. The base sequences of primers, hybridization probes, and competing probes are listed in Table 5. In (I) to (IV), the target mutations to be detected were base deletions or insertions and thus no competing probe was used. In addition, in (III) to (V) no probe for detecting the normal base sequence was used because even a patient of heterozygote of the mutation in question shows the symptom, indicating no clinical need of investigating the presence or absence of the gene having the normal base sequence.

TABLE 5

(I) Primers and probes for detection of delta F508 deletion mutation in the gene of cystic fibrosis transmembrane regulator protein
PCR forward primer:

5'-ATTATGCCTGGCACCATTAAAG-3'            (SEQ ID NO: 47)

PCR reverse primer:

5'-Dig-CATTCACAGTAGCTTACCCA-3'          (SEQ ID NO: 48)

Biotin-labeled oligonucleotide for detection of normal base sequence:

5'-AATATCATTGGTGTT-Biotin-3'            (SEQ ID NO: 49)

Biotin-labeled oligonucleotide for detection of mutant base sequence:

5'-TATCATCTTTGGTG-Biotin-3' (SEQ ID NO: 50)

(II) Primers and probes for detection of 1277insTATC insertion mutation in HEXA gene of Tay-Sachs disease
PCR forward primer:

5'-CCAGGAATCTCCTCAGCTTTGTGT-3'          (SEQ ID NO: 51)

PCR reverse primer:

5'-Dig-AGCCTCCTTTGGTTAGCAAGG-3'         (SEQ ID NO: 52)

Biotin-labeled oligonucleotide for detection of normal base sequence:

5'-TATATCTATCCTATG-Biotin-3'            (SEQ ID NO: 53)

Biotin-labeled oligonucleotide for detection of mutant base sequence:

5'-GTATATCCTATGG-Biotin-3'              (SEQ ID NO: 54)

TABLE 5-continued (III) Primers and probes for detection of 5382insC
insertion mutation in BRCA1 gene of breast cancer
PCR forward primer:

5'-CTTTCAGCATGATTTTGAAGTC-3'     (SEQ ID NO: 55)

PCR reverse primer:

5'-Dig-GGGAGTGGAATACAGAGTGG-3'   (SEQ ID NO: 56)

Biotin-labeled oligonucleotide for detection of
mutant base sequence:

5'-AGAATCCCCAGGA-Biotin-3'       (SEQ ID NO: 57)

(IV) Primers and probes for detection of 6174delT
deletion mutation in BRCA2 gene of breast cancer
PCR forward primer:

5'-GATGAATGTAGCACGCATTC-3'       (SEQ ID NO: 58)

PCR reverse primer:

5'-Dig-TCTTGTGAGCTGGTCTGAA-3'    (SEQ ID NO: 59)

Biotin-labeled oligonucleotide for detection of
mutant base sequence:

5'-ACAGCAAGGGAAAAT-Biotin-3'     (SEQ ID NO: 60)

(V) Primers and probes for detection of G1691A
mutation in blood coagulation factor V gene of
thrombosis
PCR forward primer:

5'-GGTTCCAAGTAGAATATTTAAAGAA-3'  (SEQ ID NO: 61)

PCR reverse primer:

5'-Dig-CCATTATTTAGCCAGGAGACCT-3' (SEQ ID NO: 62)

Biotin-labeled oligonucleotide for detection of
mutant base sequence:

5'-ACAGGCAAGGAA-Biotin-3'        (SEQ ID NO: 63)

TABLE 5-continued

Unlabeled competing oligonucleotide for detection
of mutant base sequence:

5'-ACAGGCGAGGAA-3'               (SEQ ID NO: 64)

All the PCR conditions or conditions including the concentrations of probes were the same as those of Example 1 in any cases of detecting the mutations described above, except that the above primers and probes must be used.

Figure 9:
FIG. 9 shows the result of the detection (chromatogram images) of a variety of mutations.

The detections, as carried out under those conditions, showed the correct determination of genotypes in all of the detection systems (FIG. 9). In each of the reactions, no false positive was observed.

The determination of genotype was completed within 10 minutes after the completion of reaction in the thermal cycler. Even at least two years after the test strip was dried without any treatment and stored at room temperature, a macroscopic determination thereof was possible.

The above-mentioned results show that the detection method of the invention enables the simple and quick detection of mutations including insertion and deletion mutations to determine the genotype of sample DNA, even though the design of primers and hybridization probes and competing probes and the reaction conditions are required to be adjusted slightly for and depending on the respective gene mutations. Therefore, it is concluded that the detection method of the present invention can be used for many purposes.

INDUSTRIAL APPLICABILITY

According to the present invention, the identification of pathogenic gene mutation and the detection of polymorphisms of disease-related genes and drug metabolism enzyme genes can be carried out in a simple, quick and accurate manner without use of other special devices and equipments than a conventional thermal cycler. The detection method of the present invention allows of the detection at bed side and is thus considered to facilitate the tailor-made medicine.

The invention claimed is:

1. A method of detecting a first sequence or a second sequence in a target region of DNA, comprising:
(A) providing a double stranded DNA comprising a target region, the target region comprising either a first sequence or a second sequence differing at a mutation site;
(B) amplifying the double stranded DNA in a first reaction mixture by a DNA polymerase reaction comprising
   (i) a first DNA polymerase,
   (ii) a first primer complementary to a second strand of the double stranded DNA and labeled with a first labeling agent,
   (iii) a second primer complementary to a first strand of the double stranded DNA,
   (iv) a first hybridization probe labeled with a second labeling agent and designed not to inhibit the DNA amplification, the first hybridization probe comprising
      a length of 10-15 mer,
      the first sequence mutation site, and
      full complementarity to the first strand of the double stranded DNA comprising the first sequence and
   (v) a second hybridization probe not labeled with the second labeling agent and designed not to inhibit the DNA amplification, the second hybridization probe comprising
      a length of 10-15 mer;
      the second sequence mutation site, and
      full complementarity to the first strand of the double stranded DNA comprising the second sequence,
   thereby obtaining a first amplified DNA comprising the first labeling agent; and
(C) hybridizing at 25° C. the first amplified DNA in the first reaction mixture to the first hybridization probe or the second hybridization probe, wherein hybridizing occurs in the first reaction mixture and no addition of a reagent occurs between amplifying and hybridizing;
(D) applying the first reaction mixture after hybridization onto a first chromatography support; and
(E) amplifying the double stranded DNA in a second reaction mixture by a DNA polymerase reaction comprising
   (i) a second DNA polymerase,
   (ii) the first primer labeled with the first labeling agent,
   (iii) the second primer,
   (iv) the first hybridization probe not labeled with the second labeling agent, and
   (v) the second hybridization probe labeled with the second labeling agent,
thereby, obtaining a second amplified DNA comprising the first labeling agent; and
(F) hybridizing at 25° C. the second amplified DNA in the second reaction mixture to the first hybridization probe or the second hybridization probe, wherein hybridizing occurs in the second reaction mixture and no addition of a reagent occurs between amplifying and hybridizing;
(G) applying the second reaction mixture after hybridization onto a second chromatography support; and
(H) determining that the DNA comprises the first sequence by detecting a first hybrid via affinity chromatography on the first chromatography support, the first hybrid being fully complementary between (i) the first hybridization probe labeled with the second labeling agent and (ii) DNA comprising the first sequence labeled with the first labeling agent; or
(I) determining that the DNA comprises the second sequence by detecting a second hybrid via affinity chromatography on the second chromatography support, the second hybrid being fully complementary between (i) the second hybridization probe labeled with the second labeling agent and (ii) DNA comprising the second sequence labeled with the first labeling agent,
wherein, a ligase enzyme is not required after hybridization.

2. The method according to claim 1, wherein a mutation of the mutation site is a point mutation, and the second hybridization probe in the first reaction mixture and the first hybridization probe in the second reaction mixture are comprised in an amount sufficient to enhance specificity of hybridization of the first amplified DNA and the second amplified DNA to the first hybridization probe and the second hybridization probe.

3. The method according to claim 1, wherein the DNA amplifications are carried out by PCR.

4. The method according to claim 1 wherein the first hybridization probe and the second hybridization probe are 10-13 mers.

5. The method according to claim 4 wherein the first hybridization probe and the second hybridization probe are 11-13 mers.

6. The method according to claim 5 wherein the first hybridization probe is a 12 mer or a 13 mer and the second hybridization probe is a 12 mer or a 13 mer.

7. The method according to claim 1 wherein the length of the first hybridization probe and the second hybridization probe are selected so that hybridization to the first amplified DNA and the second amplified DNA, respectively, does not occur at a temperature at which the first DNA polymerase and the second DNA polymerase are actively amplifying the double stranded DNA.

8. The method according to claim 1 wherein a mutation of the mutation site is an insertion mutation.

9. The method according to claim 1 wherein a mutation of the mutation site is a deletion mutation.

10. The method according to claim 1 wherein the second hybridization probe in the first reaction mixture contains a sequence complimentary to the mutation site of the target region at a middle of the second hybridization probe and the first hybridization probe in the second reaction mixture contains a sequence complimentary to the mutation site of the target region at a middle of the first hybridization probe.

11. The method according to claim 1 wherein the first hybridization probe and the second hybridization probe are 10 mers.

12. The method according to claim 1 wherein the first hybridization probe and the second hybridization probe are 11 mers.

13. The method of claim 1, wherein no addition of a reagent occurs between hybridizing and applying the first reaction mixture on to the first chromatography support and applying the second reaction mixture on to the second chromatography support.

* * * * *